(12) United States Patent
Ledoussal et al.

(10) Patent No.: US 7,868,021 B2
(45) Date of Patent: *Jan. 11, 2011

(54) ANTIMICROBIAL QUINOLONES, THEIR COMPOSITIONS AND USES

(75) Inventors: Benoit Ledoussal, Mason, OH (US); Ji-In Kim Almstead, Holmdel, NJ (US); Jeffery Lyle Gray, Loveland, OH (US)

(73) Assignee: Warner Chilcott Company, LLC, Fajardo, PR (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/338,271

(22) Filed: Dec. 18, 2008

(65) Prior Publication Data

US 2009/0111851 A1    Apr. 30, 2009

Related U.S. Application Data

(63) Continuation of application No. 11/301,685, filed on Dec. 13, 2005, now Pat. No. 7,482,454, which is a continuation of application No. 11/003,588, filed on Dec. 3, 2004, now Pat. No. 7,019,143, which is a continuation of application No. 10/392,476, filed on Mar. 18, 2003, now Pat. No. 6,849,740, which is a continuation of application No. 10/085,786, filed on Feb. 28, 2002, now abandoned, which is a continuation of application No. 09/929,943, filed on Aug. 15, 2001, now Pat. No. 6,387,928, which is a continuation-in-part of application No. 09/266,197, filed on Mar. 10, 1999, now Pat. No. 6,329,391, which is a continuation-in-part of application No. 09/139,859, filed on Aug. 25, 1998, now abandoned.

(60) Provisional application No. 60/058,891, filed on Sep. 15, 1997.

(51) Int. Cl.
*A61K 31/04*    (2006.01)
*C07D 215/38*    (2006.01)

(52) U.S. Cl. ...................... 514/312; 546/156

(58) Field of Classification Search .......... 546/156; 514/312

See application file for complete search history.

(56) References Cited

U.S. PATENT DOCUMENTS

| | | | |
|---|---|---|---|
| 4,017,622 A | 4/1977 | Minami et al. |
| 4,341,784 A | 7/1982 | Matsumoto et al. |
| 4,448,962 A | 5/1984 | Irikura et al. |
| 4,544,658 A | 10/1985 | Petersen et al. |
| 4,544,747 A | 10/1985 | Ishikawa et al. |
| 4,665,079 A | 5/1987 | Culbertson et al. |
| 4,771,054 A | 9/1988 | Domagala et al. |
| 4,780,468 A | 10/1988 | Bridges et al. |
| 4,822,801 A | 4/1989 | Domagala et al. |
| 4,844,902 A | 7/1989 | Grohe |
| 4,855,292 A | 8/1989 | Ueda et al. |
| 4,894,458 A | 1/1990 | Masuzawa et al. |
| 4,894,578 A | 1/1990 | Masuzawa et al. |
| 4,920,120 A | 4/1990 | Domagala et al. |
| 4,988,709 A | 1/1991 | Ogata et al. |
| 4,990,517 A | 2/1991 | Petersen et al. |
| 4,994,599 A | 2/1991 | Chu |
| 4,997,943 A | 3/1991 | Iwata et al. |
| 5,043,450 A | 8/1991 | Masuzawa et al. |
| 5,051,509 A | 9/1991 | Nagano et al. |
| 5,072,001 A | 12/1991 | Hagen et al. |
| 5,098,912 A | 3/1992 | Hayakawa et al. |
| 5,116,834 A | 5/1992 | Domagala et al. |
| 5,229,396 A | 7/1993 | Brighty |
| 5,281,612 A | 1/1994 | Domagala et al. |
| 5,286,723 A | 2/1994 | Hawakawa et al. |
| 5,328,908 A | 7/1994 | Demuth, Jr. et al. |
| 5,348,961 A | 9/1994 | Iwata et al. |
| 5,364,861 A | 11/1994 | Hagen et al. |
| 5,387,748 A | 2/1995 | Demuth, Jr. et al. |
| 5,412,098 A | 5/1995 | Yasuhiro et al. |
| 5,457,104 A | 10/1995 | Bartel et al. |
| 5,464,796 A | 11/1995 | Petersen et al. |
| 5,480,879 A | 1/1996 | Petersen et al. |
| 5,519,016 A | 5/1996 | Kimura et al. |
| 5,547,962 A | 8/1996 | Ito et al. |
| 5,556,979 A | 9/1996 | Philipps |
| 5,563,155 A | 10/1996 | Domagala et al. |
| 5,580,872 A | 12/1996 | Chu et al. |
| 5,599,816 A | 2/1997 | Chu et al. |
| 5,648,567 A | 7/1997 | Marhold et al. |

(Continued)

FOREIGN PATENT DOCUMENTS

CA    2073993 A1    1/1993

(Continued)

OTHER PUBLICATIONS

Albrecht, "Development of Antibacterial Agents of the Nalidixic Acid Type", Prog. In Drug Research, 21 (1977) pp. 9-104.
Koga et al., "Structure-Activity Relationships of Antibacterial 6,70-- and 7,8-Disubstituted 1-Alkyl-1,4-dihyro-4-oxoquinoline-3carboxylic Acids", J. Med. Chem., 23(1980), pp. 1358-1363.

(Continued)

*Primary Examiner*—D. Margaret Seaman
(74) *Attorney, Agent, or Firm*—Fitzpatrick, Cella, Harper & Scinto

(57) ABSTRACT

Compounds having the general structure:

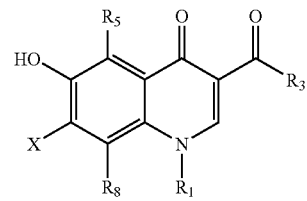

which are effective antimicrobial agents.

26 Claims, No Drawings

U.S. PATENT DOCUMENTS

| | | | |
|---|---|---|---|
| 5,656,623 | A | 8/1997 | White et al. |
| 5,726,182 | A | 3/1998 | Chu et al. |
| 5,770,597 | A | 6/1998 | Kim et al. |
| 6,235,751 | B1 | 5/2001 | Park et al. |
| 6,329,391 | B1 * | 12/2001 | Ledoussal et al. ........... 514/312 |
| 6,387,928 | B1 * | 5/2002 | Ledoussal et al. ........... 514/312 |
| 6,645,981 | B2 * | 11/2003 | Ledoussal et al. ........... 514/312 |
| 6,849,740 | B2 * | 2/2005 | Ledoussal et al. ........... 546/156 |
| 6,900,224 | B2 * | 5/2005 | Ledoussal et al. ........... 514/306 |

FOREIGN PATENT DOCUMENTS

| | | |
|---|---|---|
| CA | 2152828 A1 | 7/1994 |
| CA | 2212007 C | 7/1994 |
| CA | 2212226 A1 | 10/1995 |
| CA | 2217164 | 10/1996 |
| CA | 2238765 A1 | 5/1997 |
| CA | 2228536 | 8/1998 |
| CZ | 9201901 A3 | 1/1993 |
| CZ | 9302001 A3 | 4/1994 |
| CZ | 9400100 A3 | 3/1995 |
| EP | 0106489 A2 | 4/1984 |
| EP | 0195841 A1 | 1/1986 |
| EP | 0195316 A1 | 9/1986 |
| EP | 207 497 A2 | 1/1987 |
| EP | 230 295 | 7/1987 |
| EP | 235 762 A1 | 9/1987 |
| EP | 237 955 | 9/1987 |
| EP | 0308019 A2 | 3/1989 |
| EP | 0342675 A2 | 11/1989 |
| EP | 366 189 | 5/1990 |
| EP | 0366189 A2 | 5/1990 |
| EP | 0413455 A2 | 2/1991 |
| EP | 443 498 A1 | 8/1991 |
| EP | 500 016 A1 | 7/1993 |
| EP | 0550016 A1 | 7/1993 |
| EP | 0572259 A1 | 12/1993 |
| EP | 641 793 A1 | 3/1995 |
| EP | 0775702 A1 | 5/1997 |
| EP | 0947513 A1 | 10/1999 |
| HU | 219910 B | 3/1993 |
| IT | 1 279 532 | 1/1997 |
| JP | 51-086476 | 7/1976 |
| JP | 61-205258 A | 9/1986 |
| JP | 61-225181 A | 10/1986 |
| JP | 056673 | 8/1987 |
| JP | 62-255482 A | 11/1987 |
| JP | 64-016767 | 1/1989 |
| JP | 03-115277 A | 5/1991 |
| JP | 244733 | 8/1991 |
| JP | 05-112554 A | 5/1993 |
| JP | 05-345777 | 12/1993 |
| JP | 09-002953 A | 1/1997 |
| JP | 07-48367 A | 2/1997 |
| JP | 09-052893 A | 2/1997 |
| JP | 287669 | 4/1997 |
| JP | 09-136886 | 5/1997 |
| JP | 178847 | 6/1997 |
| JP | 240318 | 8/1997 |
| JP | 3745433 B2 | 2/2006 |
| WO | 91/16894 A1 | 11/1991 |
| WO | 95/10519 A1 | 4/1995 |
| WO | 96/39407 A1 | 12/1996 |
| WO | WO 97/19072 A1 | 5/1997 |
| WO | WO 97/29102 | 8/1997 |
| WO | 98/52939 A1 | 11/1998 |
| WO | 98/54169 A1 | 12/1998 |
| WO | 99/07696 A1 | 2/1999 |
| WO | WO 99/14214 | 3/1999 |
| WO | 00/21952 A1 | 4/2000 |
| WO | 00/78748 A1 | 12/2000 |
| WO | 01/53273 A1 | 7/2001 |
| WO | 02/48138 A1 | 6/2002 |

OTHER PUBLICATIONS

Klopman et al., "Computer Automated Structure Evaluation of Uinolong Antibacterial Agents", Antimicrob. Agents Chemother., 31(1987), pp. 1831-1840.

Wolfson et al., "The Fluoroquinolones: Structures, Mechanisms of Action and Resistance, and Specra of Activity In Vitro", Antimicrob. Agents Chemother. 28(1985), pp. 581-586.

Wentland et al., "Chap. 15. Quinolone Antibacterial Agents", Annual Reports in Medicinal Chemistry, 1986, pp. 145-154.

Cornett et al., "Chap. 14. Quinolone Antibacterial Agents", Annual Reports in Medicinal Chemistry, 1986, pp. 139-148.

Fernandes et al., "Chap. 12. Quinolones", Annual Reports in Medicinal Chemistry, 1987, pp. 117-126.

Xiam et al., "Synthesis and in Vitro Antibacterial Activity of Some 1-(Difluoromethoxyphenyl) quinolone-3-carboxylic Acids", J. Pharm. Sciences 78(1989). pp. 585-588.

Domagala et al., "7-Substituted 5-Amino-1 cyclopropyl-6,8-difluoro- 1,4-dihydro-4oxo3-quinolinecarboxylic Acids: Synthesis and Biological Activity of a New Class of Quinolone Antibacterials," J. Med. Chem. 31(1988), pp. 503-506.

Sanchez et al., "Quinolone Antibacterial Agents. Synthesis and Structure-Activity Relationships of 8-Substituted Quinoline-3-carboxylic Acids and 1,8 Naphthyridine-3-carboxylic Acids," J. Med. Chem. 31(1988), pp. 983-991.

Domagala et al., "1-Substituted 7-[3-[Ethylamino)methyl}-1 pyrrolidinyl} -6,8-difluoro-1, 4-dihyro-4oxo-3-quinoline carboyxlylic Acids. New Quantitative Structure-Activity Relationships at N 1 for the Quinolone Antibacterials", J. Med. Chem., 31(1988), pp. 991-1001.

Rosen et al., "Asymmetric Synthesis and Properties of the Enantiomers of the Antibacterial Agent 7-(3-Aminopyrrolidin-l-yl)-1-(2,4-difluorophenyl)-1,4-dihyro-6-fluoro-4-oxo-1,8-naphthyridine-3-carboxylic Acid Hydrochloride", J. Med. Chem. 31(1988), pp. 1586-90.

Rosen et al., "Desing, Synthesis, and Properties of (4S)-7-4(4Amino-2substituted-pyrrolidin l-yl) quinolone-3-carboxylic Acids", J. Med. Chem., 31(1988), pp. 1598-1611.

Bouzard et al., "Fluoronaphthyridines and Quinolones as Antibacterial Agents. 1. Synthesis and Structure-Activity Relationships of New 1-Substituted Derivates", J. Med. Chem. 32(1989), pp. 537-542.

Ledoussal et al., "Potent Non-6-fluoro-Substituted Quinolone Antibacterials: Synthesis and Biological Activitiy", J. Med. Chem., 35(1992), pp. 198-200.

Domagala et al., "Quinolone Antibacterials Containing the New 7-[3-(1-aminoethyl)-1 pyrrolidinyl] Side Chain: The Effects of the 1-Aminoethyl Moiety and its Stereochemical Configurations on Potency and in Vivo Efficacy", J. Med. Chem., 36(1993), pp. 871-882.

Hagen et al., "Synthesis and Antibacterial Activity of New Quinolones Containing a 7-[3-(1-Amino-1-methylethyl)-1-pyrrolidinyl] Moiety. Gram-Positive Agents with Excellent Oral Activity and Low Side-Effect Potential", J. Med. Chem. 37(1994), pp. 733-738.

Cecchetti et al., "Studies on 6-Aminoquinolones: Synthesis and Antibacterial Evaluation of 6-Amino-8-methylquinolones", J. Med. Chem.,, 39(1996), pp. 436-445.

Cecchetti et al, "Potent 6-Desluoro-8-methylquinolones as New Lead Compounds in Antibacterial Chemotherapy," J. Med. Chem., 39(1996) pp. 4952-4957.

Hong et al., "Novel 5-Amino-6-methylquinolone Antibacterials: a New class of Non-6-Fluoroquinolones", Bioorganic & Medicinal Chem. Letters, 7(1997), pp. 1875-1878.

Hayashi et al., "A Novel des-F(6)-Quinolone: Synthesis and In Vitro Activity of 7-(Isoindolin-5-yl) Derivatives", Abstracts in New Antimicrobials, 1997, p. 173, Poster Presentation.

Chemical Abstracts 121:157539, 1994, Abstract by Bartel.

Chemical Abstracts 130:223178, 1999, Tojima.

Chemical Abstracts 130:1294998, 1999 Yamamoto.

Chemical Abstracts 129:343410, 1998 Takemura.

Chemical Abstracts 129:153244, 1998, Sawa.
Chemical Abstracts 126:26361 1996, Cecchetti.
Chemical Abstracts 121:157629, 1994, Philipps.
Chemical Abstracts 121:157304, 1994, Marhold.
Marpat 126:31574, Lerchen, 1996.
Marpat 121:57343, Kimura, 1993.
Marpat 119:56157, Nimura, 1993.
Marpat 111:153779, Chiba, 1989.
Tabarrini, Oriana et al., "6-Hydroxy Derivative as New Deslfuoroquinolone (DFQ): Synthesis and DNA-Binding Study", Nucleosides, Nucleotides & Nucleic Acids, vol. 19(8), 2000, pp. 1327-1336.
Chemical Abstracts 96:47559, Otsuka (1981).
Chemical Abstracts 120:298485, Ito (1993).
De Sarro, A. et al. "Effects of Novel 6-Desfluoroquinolones and Classic Quinolones on Pentylenetetrazole-Induced Seizures in Mice." Antimicrobial Agents Chemotherapy, pp. 1729-1736 (Jul. 1999).
Hanessian, S. et al. "1,3-Asymmetric Induction in Dianionic Allylation Reactions of Amino Acid Derivatives—Synthesis of Functionally Useful Enantiopure Glutamates, Pipecolates and Pyroglutamates," Tetrahydron Letters, vol. 39, pp. 5887-5890 (1998).

Marpat 130:124998, Yamamoto (1999).
USPatFull 95:90528, Bartel (1995).
USPatFull 97:61894, Marhold (1997).
Suto, M.J. et al., "Fluoroquinolones: Relationships between Structural Variations, Mammalian Cell Cytotoxicity, and Antimicrobial Activity", J. Med. Chem., vol. 35, No. 25, pp. 4745-4750 (1992).
Li, Q. et al., "Synthesis and Structure—Activity Relationships of 2-Pyridones: A Novel Series of Potent DNA Gyrase Inhibitors as Antibacterial Agents", J. Med. Chem., vol. 39, pp. 3070-3088 (1996).
Sanders, Jr., W.E. et al., "Inducible beta-Lactamases: Clinical and Epidemiologic Implications for Use of Newer Cephalosporins", Reviews of Infectious Diseases, vol. 10, No. 4, pp. 830-838 (Jul.-Aug. 1988).
Ma, Z. et al., "Synthesis and Antimicrobial Activity of 4H-4-Oxoquinolizine Derivatives: Consequences of Structural Modification at the C-8 Position", J. Med. Chem., vol. 42, No. 20, pp. 4202-4213 (1999).
Jaen-Oltra, J. et al., "Artifical Neural Network Applied to Prediction of Fluorquinolone Antibacterial Activity by Topological Methods", J. Med. Chem., vol. 43, No. 6, pp. 1143-1148 (2000).

* cited by examiner

ANTIMICROBIAL QUINOLONES, THEIR COMPOSITIONS AND USES

CROSS REFERENCE TO RELATED APPLICATIONS

This application is a continuation of U.S. application Ser. No. 11/301,685, filed Dec. 13, 2005, now U.S. Pat. No. 7,482,454 which is a continuation of U.S. application Ser. No. 11/003,588, filed 3 Dec. 2004, now U.S. Pat. No. 7,019,143 which is a continuation of U.S. application Ser. No. 10/392,476 filed Mar. 18, 2003, U.S. Pat. No. 6,849,740, which is a continuation of U.S. application Ser. No. 10/085,786, filed Feb. 28, 2002, abandoned Apr. 17, 2003, which is a continuation of U.S. application Ser. No. 09/929,943 filed Aug. 15, 2001, U.S. Pat. No. 6,387,928, which is a continuation-in-part application of U.S. application Ser. No. 09/266,197, filed Mar. 10, 1999, U.S. Pat. No. 6,329,391, which is a continuation-in-part of U.S. application Ser. No. 09/139,859, filed Aug. 25, 1998, abandoned, which claims priority under Title 35, United States Code 119(e) from Provisional Application Ser. No. 60/058,891, filed Sep. 15, 1997, all of which are herein incorporated by reference in their entirety.

FIELD OF THE INVENTION

The subject invention relates to novel antimicrobial compounds, their compositions and their uses.

BACKGROUND

The chemical and medical literature describes compounds that are said to be antimicrobial, i.e., capable of destroying or suppressing the growth or reproduction of microorganisms, such as bacteria. For example, such antibacterials and other antimicrobials are described in *Antibiotics, Chemotherapeutics, and Antibacterial Agents for Disease Control* (M. Grayson, editor, 1982), and E. Gale et al., *The Molecular Basis of Antibiotic Action* 2d edition (1981).

The mechanism of action of these antibacterials vary. However, they are generally believed to function in one or more of the following ways: by inhibiting cell wall synthesis or repair; by altering cell wall permeability; by inhibiting protein synthesis; or by inhibiting synthesis of nucleic acids. For example, beta-lactam antibacterials act through inhibiting the essential penicillin binding proteins (PBPs) in bacteria, which are responsible for cell wall synthesis. As another example, quinolones act, at least in part, by inhibiting synthesis of DNA, thus preventing the cell from replicating.

The pharmacological characteristics of antimicrobials, and their suitability for any given clinical use, vary. For example, the classes of antimicrobials (and members within a class) may vary in 1) their relative efficacy against different types of microorganisms, 2) their susceptibility to development of microbial resistance and 3) their pharmacological characteristics, such as their bioavailability, and biodistribution. Accordingly, selection of an appropriate antibacterial (or other antimicrobial) in a given clinical situation requires analysis of many factors, including the type of organism involved, the desired method of administration, the location of the infection to be treated and other considerations.

However, many such attempts to produce improved antimicrobials yield equivocal results. Indeed, few antimicrobials are produced that are truly clinically-acceptable in terms of their spectrum of antimicrobial activity, avoidance of microbial resistance, and pharmacology. Thus there is a continuing need for broad spectrum antimicrobials, which are effective against resistant microbes.

Some 1,4-dihydroquinolone, naphthyridine or related heterocyclic moieties are known in the art to have antimicrobial activity and are described in the following references: R. Albrecht, *Prog. Drug Research*, Vol. 21, p. 9 (1977); J. Wolfson et al., "The Fluoroquinolones: Structures, Mechanisms of Action and Resistance, and Spectra of Activity In Vitro", *Antimicrob. Agents and Chemother.*, Vol. 28, p. 581 (1985); G. Klopman et al., *Antimicrob. Agents and Chemother.*, Vol. 31, p. 1831 (1987); M. P. Wentland et al., *Ann. Rep. Med. Chem.*, Vol. 20, p. 145 (1986); J. B. Cornett et al., *Ann. Rep. Med. Chem.*, Vol. 21, p. 139 (1986); P. B. Fernandes et al., *Ann. Rep. Med. Chem.*, Vol. 22, p. 117 (1987); A. Koga, et al., "Structure-Activity Relationships of Antibacterial 6,7- and 7,8-Disubstituted 1-alkyl-1,4-dihydro-4-oxoquinoline-3-carboxylic Acids", *J. Med. Chem.*, Vol. 23, pp. 1358-1363 (1980); J. M. Domagala et al., *J. Med. Chem.*, Vol. 31, p. 991 (1988); T. Rosen et al., *J. Med. Chem.*, Vol. 31, p. 1586 (1988); T. Rosen et al., *J. Med. Chem.*, Vol. 31, p. 1598 (1988); B. Ledoussal et al., "Non 6-Fluoro Substituted Quinolone Antibacterials: Structure and Activity", *J. Med Chem.*, Vol. 35, p. 198-200 (1992); J. M. Domagala et al., "Quinolone Antibacterials Containing the New 7-[3-(1-Aminoethyl)-1-pyrrolidinyl] Side Chain: The Effects of the 1-Aminoethyl Moiety and Its Stereochemical Configurations on Potency and in Vivo Efficacy", *J. Med. Chem.*, Vol. 36, pp. 871-882 (1993); Hagen et al., "Synthesis and Antibacterial Activity of New Quinolones Containing a 7-[3-(1-Amino-1-methylethyl)-1-pyrrolidinyl] Moiety. Gram Positive Agents with Excellent Oral Activity and Low Side-Effect Potential", *J. Med. Chem.* Vol. 37, pp. 733-738 (1994); V. Cecchetti et al., "Studies on 6-Aminoquinolines: Synthesis and Antibacterial Evaluation of 6-Amino-8-methylquinolones", *J. Med. Chem.*, Vol. 39, pp. 436-445 (1996); V. Cecchetti et al., "Potent 6-Desfluoro-8-methylquinolones as New Lead Compounds in Antibacterial Chemotherapy", *J. Med. Chem.*, Vol. 39, pp. 4952-4957 (1996); Hong et al., "Novel 5-Amino-6-methylquinolone Antibacterials: a New Class of Non-6-fluoroquinolones", *Bioorg. of Med. Chem. Let.*, Vol. 7, pp. 1875-1878 (1997); U.S. Pat. No. 4,844,902 to Grohe on Jul. 4, 1989; U.S. Pat. No. 5,072,001 to Hagen & Suto on Dec. 10, 1991; U.S. Pat. No. 5,328,908 to Demuth & White on Jul. 12, 1994; U.S. Pat. No. 5,457,104 to Bartel et al. on Oct. 10, 1995; U.S. Pat. No. 5,556,979 to Philipps et al. on Sep. 17, 1996; European Patent Appl. 572,259 of Ube Ind. pub. Dec. 1, 1993; European Patent Appl. 775,702 of Toyama Chem. Co. pub. May 28, 1997; Japanese Patent Pub. 62/255,482 of Kyorin Pharm. Co. pub. Mar. 1, 1995.

Structure activity relationships of the quinolones have been the subject of detailed study for more than a decade. As a result of these studies, it has been determined by those in the art that certain structures, with specific sites on the quinolone ring functionalized, have distinct advantages over others. For example, A. Koga, et al., "Structure-Activity Relationships of Antibacterial 6,7- and 7,8-Disubstituted 1-alkyl-1,4-dihydro-4-oxoquinoline-3-carboxylic Acids", *J. Med. Chem*, Vol. 23, pp. 1358-1363 (1980) (Koga) discloses the non-equivalence of the 6- and 8-quinolonyl position, and the importance of the substitution at the 6-quinolonyl position. Koga appears to demonstrate by examples that 6-fluoro, 8-hydrogen substitution is superior to 6-hydrogen, 8-fluoro or halo. Perhaps as a result of this early structure activity work in this area, the art has focused on the 6-fluorinated structures to provide the next generation of quinolones. Despite the work in this area, the full promise of the quinolones as antibacterials has not yet been exploited.

Examples of bacterial infections resistant to antibiotic therapy have been reported in the past; they are now a significant threat to public health in the developed world. The development of microbial resistance (perhaps as a result of the intense use of antibacterials over extended periods of time) is of increasing concern in medical science. "Resistance" can be defined as existence of organisms, within a population of a given microbial species, that are less susceptible to the action of a given antimicrobial agent. This resistance is of particular concern in environments such as hospitals and nursing homes, where relatively high rates of infection and intense use of antibacterials are common. See, e.g., W. Sanders, Jr. et al., "Inducible Beta-lactamases: Clinical and Epidemiologic Implications for Use of Newer Cephalosporins", *Reviews of Infectious Diseases* p. 830 (1988).

Pathogenic bacteria are known to acquire resistance via several distinct mechanisms including inactivation of the antibiotic by bacterial enzymes (e.g., b-lactamases hydrolyzing penicillin and cephalosporins); removal of the antibiotic using efflux pumps; modification of the target of the antibiotic via mutation and genetic recombination (e.g., penicillin-resistance in *Neiserria gonorrhoeae*); and acquisition of a readily transferable gene from an external source to create a resistant target (e.g., methicillin-resistance in *Staphylococcus aureus*). There are certain Gram positive pathogens, such as vancomycin-resistant *Enterococcus faecium*, which are resistant to virtually all commercially available antibiotics.

Hence existing antibacterials have limited capacity in overcoming the threat of resistance. Thus it would be advantageous to provide a quinolone with useful properties that can be used commercially against resistant microbes.

OBJECTS OF THE INVENTION

It is an object of the subject invention to provide quinolone and quinolonyl antimicrobial compounds that are useful against a broad spectrum of microbes, and especially against bacteria.

It is a further object of the invention to provide such antimicrobials which are effective against quinolone-resistant microbes.

SUMMARY OF THE INVENTION

We have found a novel series of quinolone and quinolonyl compounds that are effective against resistant microbes, and provide significant activity advantages over the art. Furthermore, we have found that these quinolone and quinolonyl compounds defy the art accepted structure/activity relationships.

The invention relates to compounds of formula

Formula 1

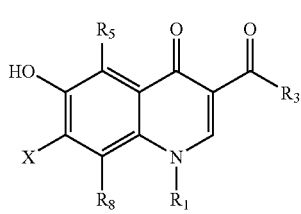

wherein:
(a) X is selected from

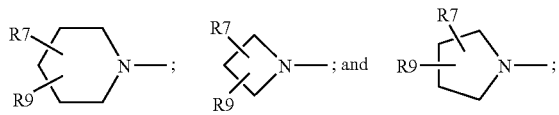

(b) $R_1$ is selected from $C_3$ to about $C_5$ cycloalkyl, $C_1$ to about $C_2$ alkanyl, $C_2$ to about $C_3$ linear alkenyl, $C_3$ to about $C_4$ branched alkanyl or alkenyl, all such alkyl or cycloalkyl moieties being unsubstituted or substituted with from 1 to about 3 fluoro; and phenyl, unsubstituted or substituted with from 1 to about 3 fluoro, or with one hydroxy in the 4-position;
(c) $R_3$ is hydrogen or hydroxy;
(d) $R_5$ is selected from hydrogen, hydroxy, amino, halo, $C_1$ to about $C_2$ alkanyl, $C_2$ alkenyl, and methoxy, all alkyl moieties being unsubstituted or substituted with from 1 to about 3 fluoro;
(e) $R_8$ is selected from the group consisting of fluoro, chloro and bromo;
(f) $R_7$ is amino which is attached to a ring carbon of X which is not adjacent to the ring nitrogen, the amino being unsubstituted or substituted with one or two $C_1$ to about $C_3$ alkanyl; or aminoalkanyl which is attached to any ring carbon of X and is $C_1$ to about $C_3$ alkanyl substituted with one amino, the amino being unsubstituted or substituted with one or two $C_1$ to about $C_3$ alkanyl;
(g) each $R_9$ is independently selected from hydrogen, $C_1$ to about $C_4$ alkanyl, $C_2$ to about $C_6$ alkenyl or alkynyl, and a $C_3$ to about $C_6$ fused or spirocycle alkyl ring; one $R_9$ is optionally selected from hydroxy, $C_1$ to about $C_4$ alkoxy, aryl, and heteroaryl; all alkyl and aryl portions of R9 moieties being unsubstituted or substituted with one hydroxy or with from 1 to about 3 fluoro; and
(h) a $R_7$ moiety described in (f) and a $R_9$ moiety described in (g) may optionally be connected thus forming a fused or spirocycle ring with the N-containing ring shown in (a), the fused or spirocycle ring comprising from 2 to about 5 ring carbons and 0 or 1 ring nitrogen, but if such rings are fused, $R_8$ is preferably other than chloro or bromo or alkyl;

or an optical isomer, diastereomer or enantiomer thereof; a pharmaceutically-acceptable salt, hydrate, or biohydrolyzable ester, amide or imide thereof. In addition, compounds incorporating the compounds of the invention, or using compounds of the invention as starting materials are also contemplated in this invention.

It has been found that the compounds of this invention, and compositions containing these compounds, are effective antimicrobial agents against a broad range of pathogenic microorganisms with advantages in low susceptibility to microbial resistance, reduced toxicity, and improved pharmacology.

Moreover, these 6-hydroxy/8-halogen compounds are of lower phototoxicity than previously disclosed 8-halogen quinolones.

DESCRIPTION OF THE INVENTION

The present invention encompasses certain compounds, dosage forms, and methods of administering the compounds to a human or other animal subject. Specific compounds and compositions to be used in the invention must, accordingly, be pharmaceutically acceptable. As used herein, such a "pharmaceutically-acceptable" component is one that is suitable for use with humans and/or animals without undue adverse side effects (such as toxicity, irritation, and allergic response) commensurate with a reasonable benefit/risk ratio.

GLOSSARY OF TERMS

Unless otherwise specified, the following terms have the indicated meanings when used in this application.

"Alkanyl" is an unsubstituted or substituted, linear or branched, saturated hydrocarbon chain radical having from 1 to 8 carbon atoms, preferably from 1 to 4 carbon atoms. Preferred alkanyl groups include (for example) methyl, ethyl, propyl, isopropyl, and butyl.

"Alkenyl" is an unsubstituted or substituted, linear or branched, hydrocarbon chain radical having from 2 to 8 carbon atoms, preferably from 2 to 4 carbon atoms, and having at least, preferably only one, one carbon-carbon double bond.

"Alkynyl" is an unsubstituted or substituted, linear or branched, hydrocarbon chain radical having from 2 to 8 carbon atoms, preferably from 2 to 4 carbon atoms, and having at least, preferably only one, one carbon-carbon triple bond.

"Alkyl" includes alkanyl, alkenyl, and alkynyl as defined above, unless specifically limited otherwise to only one or two of them or by other restrictions. Alkyl retains this meaning when it is used as part of another word; examples are provided below (e.g., alkylene, haloalkyl). In such words, alkyl can be replaced by any of alkanyl, alkenyl, or alkynyl to narrow the meaning of such words accordingly.

"Alkylene" is a hydrocarbon diradical. Preferred alkylene includes ethylene and methylene.

"Amino" is an unsubstituted or substituted —NH$_2$.

"Haloalkyl" is an alkyl with one or more halogens (fluoro, chloro, bromo, iodo) on the alkyl. Hence, fluoroalkyl is an example of a subgenus of haloalkyl.

"Heteroatom" is a nitrogen, sulfur or oxygen atom. Groups containing one or more heteroatoms may contain different heteroatoms.

"Heteroalkyl" is an unsubstituted or substituted chain radical having from 2 to 8 members comprising carbon atoms and at least one heteroatom.

"Carbocyclic ring" is an unsubstituted or substituted, saturated, unsaturated or aromatic, hydrocarbon ring radical. Carbocyclic rings are monocyclic or are fused, bridged or spiro polycyclic ring systems. Monocyclic rings contain from 3 to 9 carbon atoms, preferably 3 to 6 carbon atoms. Polycyclic rings contain from 7 to 17 carbon atoms, preferably from 7 to 13 carbon atoms.

"Cycloalkyl" is a saturated or unsaturated, but not aromatic, carbocyclic ring radical. Preferred cycloalkyl groups are saturated, and include cyclopropyl, cyclobutyl and cyclopentyl, especially cyclopropyl.

"Heterocyclic ring" is an unsubstituted or substituted, saturated, unsaturated or aromatic ring radical comprised of carbon atoms and one or more heteroatoms in the ring. Heterocyclic rings are monocyclic or are fused, bridged or spiro polycyclic ring systems. Monocyclic rings contain from 3 to 9 carbon and heteroatoms, preferably 3 to 6 carbon and heteroatoms. Polycyclic rings contain from 7 to 17 carbon and heteroatoms, preferably from 7 to 13 carbon and heteroatoms.

"Aryl" is an unsubstituted or substituted aromatic carbocyclic ring radical. Preferred aryl groups include (for example) phenyl, 2,4-difluorophenyl, 4-hydroxyphenyl, tolyl, xylyl, cumenyl and naphthyl; more preferred is phenyl. Preferred substituents for aryl include fluoro and hydroxy.

"Heteroaryl" is an unsubstituted or substituted aromatic heterocyclic ring radical. Preferred heteroaryl groups include (for example) thienyl, furyl, pyrrolyl, pyridinyl, pyrazinyl, thiazolyl, quinolinyl, pyrimidinyl and tetrazolyl.

"Alkoxy" is an oxygen radical having a hydrocarbon chain substituent, where the hydrocarbon chain is an alkyl (i.e., —O-alkyl or —O-alkanyl). Preferred alkoxy groups are saturated, and include (for example) methoxy, ethoxy, propoxy and allyloxy.

"Alkylamino" is an amino radical having one or two alkyl substituents (e.g., —NH-alkyl). The alkyl groups are preferably saturated, and include (for example) methyl and ethyl.

"Arylalkyl" is an alkyl radical substituted with an aryl group. Preferred arylalkyl groups include benzyl and phenylethyl.

"Arylamino" is an amino radical substituted with an aryl group (e.g., —NH-phenyl).

"Aryloxy" is an oxygen radical having a aryl substituent (e.g., —O-phenyl).

"Acyl" or "carbonyl" is a radical formed by removal of the hydroxy from a carboxylic acid (e.g., R—C(O)—). Preferred groups include (for example) formyl, and alkylacyl moieties such as acetyl and propionyl.

"Acyloxy" is an oxygen radical having an acyl substituent (i.e., —O-acyl); for example, —O—C(O)-alkyl.

"Acylamino" is an amino radical having an acyl substituent (e.g., —NH-acyl); for example, —NH—C(O)-alkyl.

"Halo", "halogen", or "halide" is a chloro, bromo, fluoro or iodo radical.

Also, as referred to herein, a "lower" hydrocarbon moiety (e.g., "lower" alkyl) is a hydrocarbon chain comprised of 1 to 4, preferably from 1 to 2, carbon atoms.

A "pharmaceutically-acceptable salt" is a cationic salt formed at any acidic (e.g., carboxyl) group, or an anionic salt formed at any basic (e.g., amino, alkylamino, dialkylamino, morphylino, and the like) group on the compound of the invention. Since many of the compounds of the invention are zwitterionic, either salt is possible and acceptable. Many such salts are known in the art. Preferred cationic salts include the alkali metal salts (such as sodium and potassium), alkaline earth metal salts (such as magnesium and calcium) and organic salts, such as ammonio. Preferred anionic salts include halides, sulfonates, carboxylates, phosphates, and the like. Clearly contemplated in such salts are addition salts that may provide an optical center, where once there was none. For example, a chiral tartrate salt may be prepared from the compounds of the invention, and this definition includes such chiral salts. Salts contemplated are nontoxic in the amounts administered to the patient-animal, mammal or human.

The compounds of the invention are sufficiently basic to form acid-addition salts. The compounds are useful both in the free base form and the form of acid-addition salts, and both forms are within the purview of the invention. The acid-addition salts are in some cases a more convenient form for use. In practice, the use of the salt form inherently amounts to the use of the base form of the active. Acids used to prepare acid-addition salts include preferably those which produce, when combined with the free base, medicinally acceptable salts. These salts have anions that are relatively innocuous to the animal organism, such as a mammal, in medicinal doses of the salts so that the beneficial property inherent in the free base are not vitiated by any side effects ascribable to the acid's anions.

Examples of appropriate acid-addition salts include, but are not limited to hydrochloride, hydrobromide, hydroiodide, sulfate, hydrogensulfate, acetate, trifluoroacetate, nitrate, citrate, fumarate, formate, stearate, succinate, maleate, malonate, adipate, glutarate, lactate, propionate, butyrate, tartrate, methanesulfonate, trifluoromethanesulfonate, p-toluenesulfonate, dodecyl sulfate, cyclohexanesulfamate, and the like. However, other appropriate medicinally acceptable salts within the scope of the invention are those derived from other mineral acids and organic acids. The acid-addition salts of the basic compounds are prepared by several methods. For example, the free base can be dissolved in an aqueous alcohol solution containing the appropriate acid and the salt is isolated by evaporation of the solution. Alternatively, they may be prepared by reacting the free base with an acid in an organic solvent so that the salt separates directly. Where separation of the salt is difficult, it can be precipitated with a second organic solvent, or can be obtained by concentration of the solution.

Although medicinally acceptable salts of the basic compounds are preferred, all acid-addition salts are within the scope of the present invention. All acid-addition salts are useful as sources of the free base form, even if the particular salt per se is desired only as an intermediate product. For example, when the salt is formed only for purposes of purification or identification, or when it is used as an intermediate in preparing a medicinally acceptable salt by ion exchange procedures, these salts are clearly contemplated to be a part of this invention.

"Host" is a substrate capable of sustaining a microbe, preferably it is a living organism, more preferably an animal, more preferably a mammal, more preferably still a human.

"Biohydrolyzable amides" are aminoacyl, acylamino, or other amides of the compounds of the invention, where the amide does not essentially interfere, preferably does not interfere, with the activity of the compound, or where the amide is readily converted in vivo by a host to yield an active compound.

"Biohydrolyzable imides" are imides of compounds of the invention, where the imide does not essentially interfere, preferably does not interfere, with the activity of the compound, or where the imide is readily converted in vivo by a host to yield an active compound. Preferred imides are hydroxyimides.

"Biohydrolyzable esters" are esters of compounds of the invention, where the ester does not essentially interfere, preferably does not interfere, with the antimicrobial activity of the compound, or where the ester is readily converted in a host to yield an active compound. Many such esters are known in the art, as described in U.S. Pat. No. 4,783,443, issued to Johnston and Mobashery on Nov. 8, 1988 (incorporated by reference herein). Such esters include lower alkyl esters, lower acyloxy-alkyl esters (such as acetoxymethyl, acetoxyethyl, aminocarbonyloxymethyl, pivaloyloxymethyl and pivaloyloxyethyl esters), lactonyl esters (such as phthalidyl and thiophthalidyl esters), lower alkoxyacyloxyalkyl esters (such as methoxycarbonyloxymethyl, ethoxycarbonyloxyethyl and isopropoxycarbonyloxyethyl esters), alkoxyalkyl esters, choline esters and alkylacylaminoalkyl esters (such as acetamidomethyl esters).

The illustration of specific protected forms and other derivatives of the Formula 1 compounds is not intended to be limiting. The application of other useful protecting groups, salt forms, etc. is within the ability of the skilled artisan.

"Optical isomer", "stereoisomer", "diastereomer" as referred to herein have the standard art recognized meanings (Cf., *Hawley's Condensed Chemical Dictionary*, 11th Ed.).

The compounds of the invention may have one or more chiral centers. As a result, one may selectively prepare one optical isomer, including diastereomer and enantiomer, over another, for example by use of chiral starting materials, catalysts or solvents, one may prepare both stereoisomers or both optical isomers, including diastereomers and enantiomers at once (a racemic mixture). Since the compounds of the invention may exist as racemic mixtures, mixtures of optical isomers, including diastereomers and enantiomers, or stereoisomers, they may be separated using known methods, such as chiral resolution, chiral chromatography and the like.

In addition, it is recognized that one optical isomer, including diastereomer and enantiomer, or stereoisomer may have favorable properties over the other. Thus when disclosing and claiming the invention, when one racemic mixture is disclosed, it is clearly contemplated that both optical isomers, including diastereomers and enantiomers, or stereoisomers substantially free of the other are disclosed and claimed as well.

As used herein, a quinolone derivative includes prodrugs of a quinolone, or an active drug made from a quinolone. Preferably, such derivatives include lactams (e.g., cephems, carbacephems, penems, monolactams, etc.) covalently linked to the quinolone optionally via a spacer. Such derivatives and methods to make and use them are apparent to the skilled artisan, given the teaching of this specification.

Compounds of the Invention

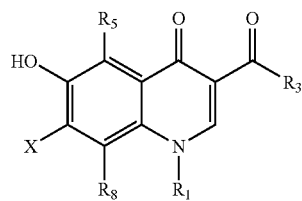

Formula 1

In Formula 1, X is selected from

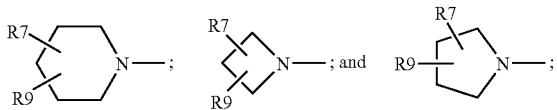

Preferred X include the pyrrolidinyl ring above or the piperidinyl ring above or the azetidinyl ring above; more preferred is the pyrrolidinyl ring; also more preferred is the piperidinyl ring.

In Formula 1, R1 includes certain alkyl, cycloalkyl, and aryl moieties. R1 cycloalkyl moieties include from about 3 to about 5 carbon atoms in the ring, preferably 3 carbon atoms in the ring. R1 cycloalkyl moieties are preferably saturated or unsaturated with one double bond; more preferably R1 cycloalkyl are saturated (cycloalkanyl). R1 linear alkanyl contain from 1 to about 2 carbon atoms; methyl and ethyl are preferred, especially ethyl. R1 linear alkenyl contain from 2 to about 3 carbon atoms; ethenyl is preferred. R1 branched alkanyl and alkenyl contain from 3 to about 4 carbon atoms; branched alkanyl are preferred; isopropyl, isopropenyl, isobutyl, isobutenyl, and t-butyl are also preferred. All of the foregoing alkyl (alkanyl, alkenyl, and alkynyl) or cycloalkyl moieties aforementioned in this paragraph are unsubstituted or substituted with from 1 to about 3 fluoro moieties. R1 aryl moieties include phenyl, unsubstituted or substituted with from 1 to about 3 fluoro, or with one hydroxy in the 4-position; substituted phenyl are preferred. Preferred R1 is selected from cyclopropyl, ethyl, phenyl substituted with 1 to 3 fluoro, and 4-hydroxyphenyl; more preferred is 2,4-difluorophenyl, and especially cyclopropyl or ethyl.

In Formula 1, R3 is hydrogen or hydroxy; preferably R3 is hydroxy. When R3 is hydroxy, it and the carbonyl to which it is attached are a carboxylic acid moiety. As such, it is a potential point of formation for the subject compounds of pharmaceutically-acceptable salts, and biohydrolizable esters, aminoacyls, and amides, as described herein. Compounds having any such variations at the R3 position are included in the subject invention.

In Formula 1, R5 includes hydrogen, amino, halo, hydroxy, methoxy, and certain alkyl. R5 alkanyl moieties have from 1 to about 2 carbon atoms, preferably 1 carbon atom. R5 alkenyl moieties preferably have 2 carbon atoms. All R5 alkyl and methoxy moieties are unsubstituted or substituted with from 1 to about 3 fluoro moieties. Preferred R5 is selected from hydrogen, hydroxy, chloro, bromo, amino, methyl, monofluoromethyl, difluoromethyl, and trifluoromethyl. More preferred R5 is selected from hydrogen, hydroxy, amino, and methyl, especially hydrogen.

In Formula 1, R8 includes fluoro, chloro, and bromo. Preferred R8 is selected from fluoro and chloro. More preferred R8 is chloro.

In X of Formula 1, R7 includes amino which is attached to a ring carbon which is not adjacent to the ring nitrogen. Such R7 amino is unsubstituted or substituted with one or two alkanyl having from 1 to about 3 carbon atoms, preferably methyl or ethyl, more preferably methyl; preferred amino R7 is unsubstituted or substituted with one such alkanyl moiety. When X comprises the piperidinyl ring, R7 is preferably an unsubstituted or substituted amino moiety, preferably attached at the 3-position or 4-position of the piperidinyl ring, more preferably at the 3-position. More preferred R7, especially when X comprises the piperidinyl ring, is amino or methylamino.

R7 also includes aminoalkanyl, the alkanyl having from 1 to about 3 carbon atoms, preferably methyl, ethyl, or isopropyl, the alkanyl being substituted with one amino, such amino being unsubstituted or substituted with 1 or 2, preferably 1, alkanyl having from 1 to about 3 carbon atoms, preferably ethyl or especially methyl. Such aminoalkanyl can be attached to any carbon of the ring of X; preferably it is attached to a carbon not adjacent to the ring nitrogen. R7 is preferably such aminoalkanyl, especially if R8 is any unsubstituted alkyl, also particularly if X comprises the pyrrolidinyl ring. Preferred R7, especially when X comprises the pyrrolidinyl ring, is selected from aminomethyl, methylaminomethyl, 1-aminoethyl, 1-methylaminoethyl, 1-amino-1-methylethyl, and 1-methylamino-1-methylethyl; such moieties are preferably attached at the 3-position of the pyrrolidinyl ring.

The amino moiety of R7 is a potential point of formation for the subject compounds of a pharmaceutically-acceptable anionic salt; such salts are included in the subject invention compounds. Preferred salts are acid addition salts with, for example, HCl, CH$_3$SO$_3$H, HCOOH, or CF$_3$COOH.

In X of Formula 1, R9 represents all the moieties other than R7 on the ring carbons of the piperidinyl, pyrrolidinyl, and azetidinyl rings of X shown above; such moieties include hydrogen, alkyl, aryl, heteroaryl, hydroxy, or alkoxy. Alkyl R9 may be mono- or disubstituents on each ring carbon atom to which R7 is not attached or mono-substituents on the ring carbon to which R7 is attached (i.e., each ring carbon of X may have two hydrogens, one hydrogen and R7, one hydrogen and one alkyl, one alkyl and R7, or two alkyls bonded to it). Preferably no more than two ring carbons have alkyl R9 substituents; more preferably only one ring carbon has alkyl R9 substituents; also preferably all R9 are hydrogen. A non-hydrogen, non-alkyl R9 (aryl, heteroaryl, hydroxy or alkoxy) may optionally be a mono-substituent on a ring carbon to which R7 is not attached. Preferably there is no more than one non-hydrogen, non-alkyl R9 for a subject compound; more preferably there are none.

Non-hydrogen R9 includes linear, branched or cyclic alkanyl, preferably linear or branched, more preferably linear, having from 1 to about 4 carbon atoms; methyl and ethyl are preferred; methyl is more preferred. Non-hydrogen R9 includes linear, branched or cyclic alkenyl and alkynyl, preferably linear or branched, more preferably linear, having from 2 to about 6 carbon atoms, preferably from 2 to about 4 carbon atoms; ethenyl is preferred. Non-hydrogen R9 includes hydroxy and linear or branched alkoxy having from 1 to about 4 carbon atoms, preferably methoxy or ethoxy. Non-hydrogen R9 includes aryl, preferably phenyl; and heteroaryl, preferably having 5 or 6 ring atoms with one or two, preferably one, heteroatom that is preferably oxygen or sulfur, more preferably thienyl or furyl.

Alkyl R9, especially dialkyl R9, are preferably attached to a carbon of the ring of X which is adjacent to the ring nitrogen, especially when X comprises the pyrrolidinyl ring. A non-hydrogen, non-alkyl R9 is preferably attached to a carbon of the ring of X which is not adjacent to the ring nitrogen. Also preferred, when X comprises the piperidinyl ring and R7 is attached to the 3-carbon of the ring, is for one non-hydrogen R9 to be attached to the 4-carbon of the ring.

Two alkyl R9 can be attached together thus forming a fused or a spirocycle alkyl ring with the N-containing ring of X, the fused or spirocycle ring having from about 3 to about 6 carbon atoms. Such fused or spirocycle alkyl ring is preferably saturated or unsaturated with one double bond, more preferably saturated. A spirocyclopropyl ring is particularly preferred.

All alkyl and aryl portions of R9 moieties are unsubstituted or substituted with one hydroxy moiety or with from 1 to about 3 fluoro moieties, preferably unsubstituted.

More preferred R9 is selected from hydrogen, methyl, dimethyl, spirocyclopropyl, and ethyl; more preferred are ethyl, dimethyl, and spirocyclopropyl; and especially hydrogen.

Optionally, an alkyl R9 can be connected to R7 thus forming a fused or a spirocycle ring with the N-containing ring of X, the fused or spirocycle ring having from 2 to about 5 ring carbon atoms and 0 or 1 ring nitrogen atom (from R7). Such fused or spirocycle ring may be a hydrocarbon ring with an amino or aminoalkyl substituent, the amino being from R7; or it may be a heterocyclic ring with the R7 amino nitrogen being a ring nitrogen. Such ring may have one or two alkanyl substituents. Such fused or spirocycle ring is preferably saturated or unsaturated with one double bond; more preferably it is saturated.

Subject compounds having R7 or R9 spirocycles are named according to the following numbering system: the numbering starts at the smaller ring, completing around the larger ring which forms a spiro junction, e.g., at carbon 3 when the smaller ring is cyclopropyl as for the following example:

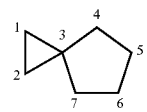

The aza nomenclature used herein follows the conventional nomenclature and is the position where the ring nitrogen is attached to the quinolone nucleus.

As used herein, any radical is independently selected each time it is used (e.g., R1 and R5 need not be the same in all occurrences in defining a given compound of this invention).

The compounds of the invention may contain chiral center(s), thus any such compound includes and contemplates each optical isomer, diastereomer or enantiomer thereof, in purified or substantially purified form, and mixtures thereof, including racemic mixtures.

The following exemplary compounds are made using the procedures described herein and variations thereof which are within the purview of the skilled artisan's practice. The examples below do not limit the invention, but rather serve to illustrate some of the embodiments of the invention.

Preferred examples of the quinolones of the subject invention with structures of Formula 2 are provided in the table below:

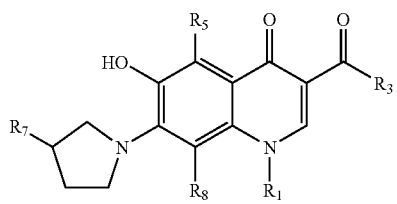

Formula 2

In the following examples, $R_1$ is cyclopropyl, $R_3$ is hydroxy, all R9 are hydrogen, and z represents the preferred chirality of the $R_7$ radical's attachment on the pyrrolidine ring, although other chirality is also envisioned. In compounds where $R_7$ is —CH(CH$_3$)NH$_2$, it is preferred that the configuration of this radical be R.

| Example | R5 | R7 | R8 | z |
|---|---|---|---|---|
| 1 | —NH2 | —NH2 | Cl | S |
| 2 | —NH$_2$ | —CH$_2$NH$_2$ | Cl | S |
| 3 | —NH$_2$ | —CH(CH$_3$)NH$_2$ | Cl | R |
| 4 | F | —NH$_2$ | Cl | S |
| 5 | F | —CH$_2$NH$_2$ | Cl | S |
| 6 | F | —CH(CH$_3$)NH$_2$ | Cl | R |
| 7 | —OCH$_3$ | —NH$_2$ | Cl | S |
| 8 | —OH | —NH$_2$ | Cl | S |
| 9 | —OH | —CH$_2$NH$_2$ | Cl | S |
| 10 | —OH | —CH(CH$_3$)NH$_2$ | Cl | R |
| 11 | H | —NH$_2$ | Cl | S |
| 12 | H | —CH$_2$NH$_2$ | Cl | S |
| 13 | H | —CH(CH$_3$)NH$_2$ | Cl | R |
| 14 | H | —CH(CH$_3$)NHCH$_3$ | Cl | R |
| 15 | H | —C(CH$_3$)$_2$NHCH$_3$ | Cl | R |
| 16 | H | —C(CH$_3$)$_2$NH$_2$ | Cl | R |
| 17 | H | —CH(CH$_3$)N(CH$_3$)$_2$ | Cl | R |
| 18 | —NH2 | —NH2 | F | S |
| 19 | —NH$_2$ | —CH$_2$NH$_2$ | F | S |
| 20 | —NH$_2$ | —CH(CH$_3$)NH$_2$ | F | R |
| 21 | F | —NH$_2$ | F | S |
| 22 | F | —CH$_2$NH$_2$ | F | S |
| 23 | F | —CH(CH$_3$)NH$_2$ | F | R |
| 24 | —OCH$_3$ | —NH$_2$ | F | S |
| 25 | —OH | —NH$_2$ | F | S |
| 26 | —OH | —CH$_2$NH$_2$ | F | S |
| 27 | —OH | —CH(CH$_3$)NH$_2$ | F | R |
| 28 | H | —NH$_2$ | F | S |
| 29 | H | —CH$_2$NH$_2$ | F | S |
| 30 | H | —CH(CH$_3$)NH$_2$ | F | R |
| 31 | H | —CH(CH$_3$)NHCH$_3$ | F | R |

-continued

| Example | R5 | R7 | R8 | z |
|---|---|---|---|---|
| 32 | H | —C(CH$_3$)$_2$NHCH$_3$ | F | R |
| 33 | H | —C(CH$_3$)$_2$NH$_2$ | F | R |
| 34 | H | —CH(CH$_3$)N(CH$_3$)$_2$ | F | R |
| 35 | —NH2 | —NH2 | Br | S |
| 36 | —NH$_2$ | —CH$_2$NH$_2$ | Br | S |
| 37 | —NH$_2$ | —CH(CH$_3$)NH$_2$ | Br | R |
| 38 | F | —NH$_2$ | Br | S |
| 39 | F | —CH$_2$NH$_2$ | Br | S |
| 40 | F | —CH(CH$_3$)NH$_2$ | Br | R |
| 41 | —OCH$_3$ | —NH$_2$ | Br | S |
| 42 | —OH | —NH$_2$ | Br | S |
| 43 | —OH | —CH$_2$NH$_2$ | Br | S |
| 44 | —OH | —CH(CH$_3$)NH$_2$ | Br | R |
| 45 | H | —NH$_2$ | Br | S |
| 46 | H | —CH$_2$NH$_2$ | Br | S |
| 47 | H | —CH(CH$_3$)NH$_2$ | Br | R |
| 48 | H | —CH(CH$_3$)NHCH$_3$ | Br | R |
| 49 | H | —C(CH$_3$)$_2$NHCH$_3$ | Br | R |
| 50 | H | —C(CH$_3$)$_2$NH$_2$ | Br | R |

Preferred examples of the quinolones of the subject invention with structures of Formula 1 are provided in the table below.

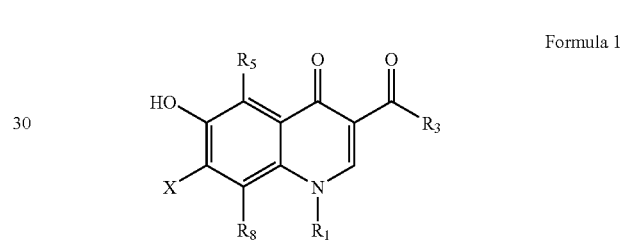

Formula 1

In the following examples, R3 is hydroxy, R5 is hydrogen, and z represents the preferred chirality, if any, of attachment of the R7 radical to the respective pyrrolidine or piperidine ring, although other chirality is also envisioned.

| Example | R8 | R1* | X* | z |
|---|---|---|---|---|
| 51 | —F | cyclopropyl | H$_2$N-azetidinyl | — |
| 52 | —Cl | cyclopropyl | H$_2$N-azetidinyl | — |
| 53 | —Br | cyclopropyl | H$_2$N-azetidinyl | — |
| 54 | —F | cyclopropyl | H$_2$N-CH$_2$-azetidinyl | — |
| 55 | —Cl | cyclopropyl | H$_2$N-CH$_2$-azetidinyl | — |
| 56 | —Br | cyclopropyl | H$_2$N-CH$_2$-azetidinyl | — |
| 57 | —F | cyclopropyl | H$_2$N-C(Me)$_2$-azetidinyl | — |
| 58 | —Cl | cyclopropyl | H$_2$N-C(Me)$_2$-azetidinyl | — |
| 59 | —Br | cyclopropyl | H$_2$N-C(Me)$_2$-azetidinyl | — |
| 60 | —F | cyclopropyl | H$_2$N-piperidinyl | — |
| 61 | —Cl | cyclopropyl | H$_2$N-piperidinyl | — |
| 62 | —Br | cyclopropyl | H$_2$N-piperidinyl | — |
| 62 | —F | cyclopropyl | H$_2$N-piperidinyl | S |
| 63 | —Cl | cyclopropyl | H$_2$N-piperidinyl | S |
| 64 | —Br | cyclopropyl | H$_2$N-piperidinyl | S |

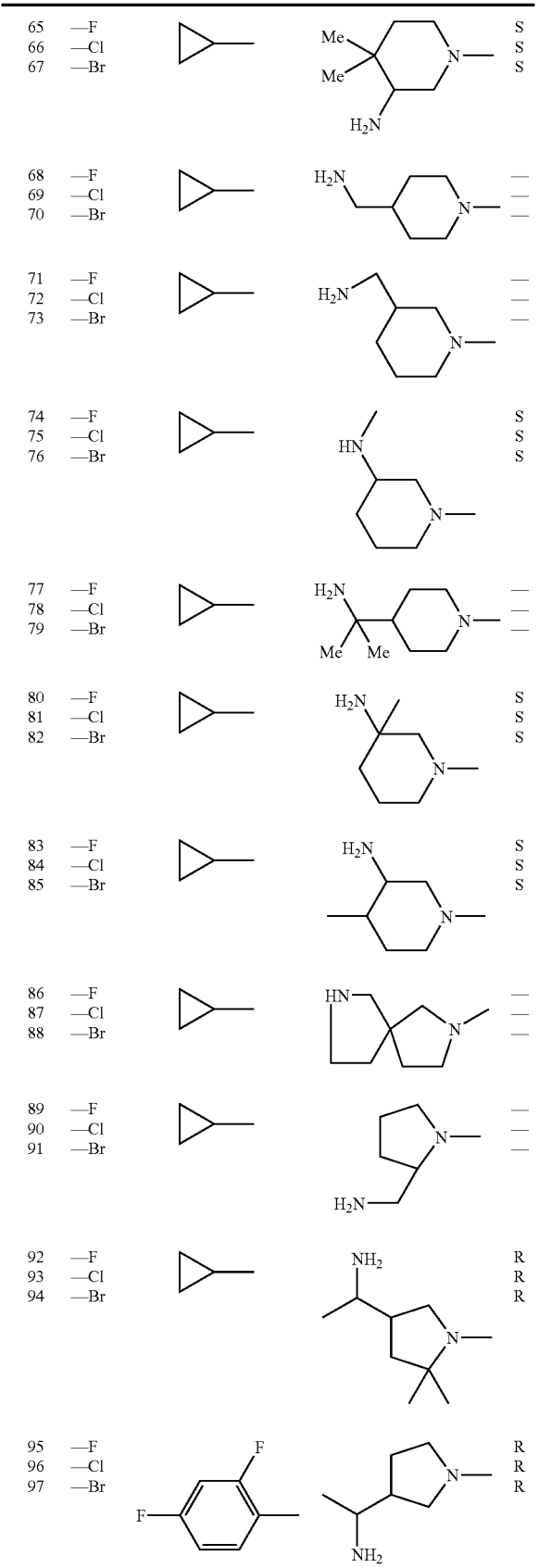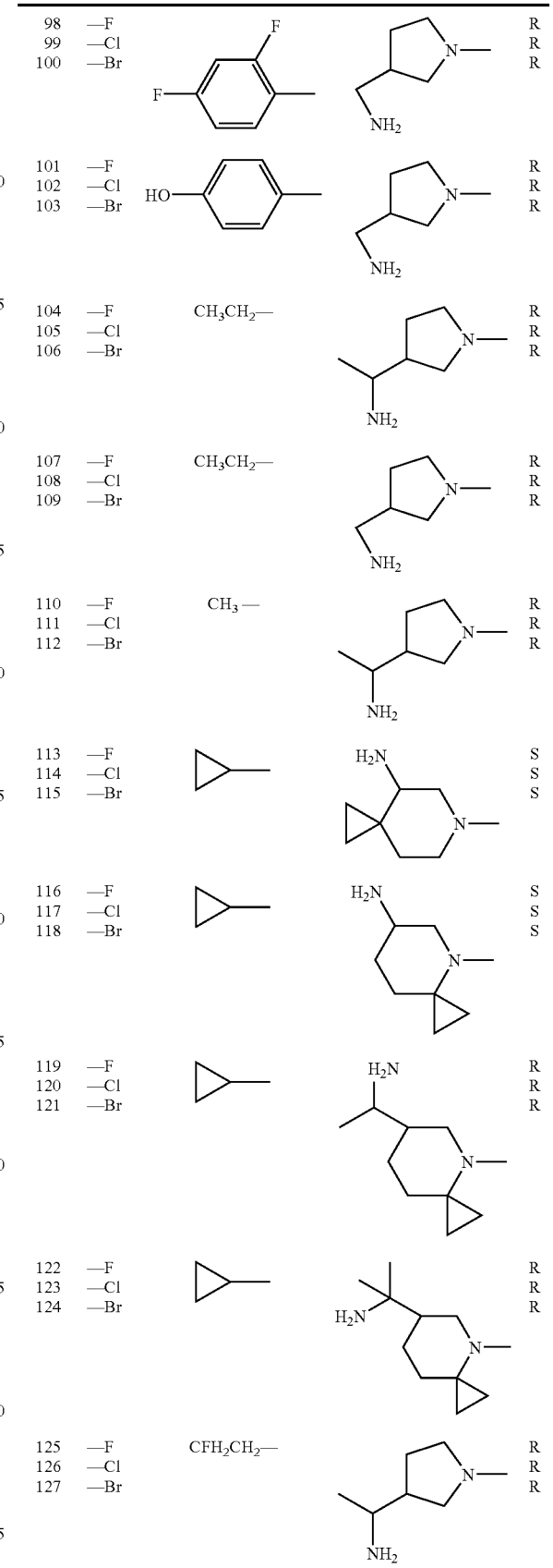

| 128 | —F  |
| 129 | —Cl |
| 130 | —Br |

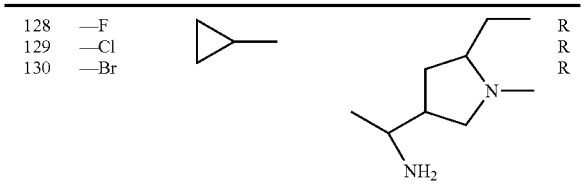

*Each structure depicted in this column generally pertains to the two or three different Examples with which it is grouped.

In addition, it is recognized that for purification, administration and the like, salts and other derivatives of the above compounds are often used. Thus, a pharmaceutically-acceptable salt, hydrate, or biohydrolyzable ester, amide or imide thereof is contemplated as part of the subject invention.

The subject invention compounds above are also useful precursors for compounds of formula Q-L-B, wherein Q is a compound of Formula 1, L is a linking moiety, and B is a lactam containing moiety. This formula includes optical isomers, disatereomers or enantiomers thereof, pharmaceutically-acceptable salts, hydrates, or biohydrolyzable esters, amides and imides thereof. These compounds and their uses are disclosed in U.S. Pat. No. 5,180,719 issued Jan. 19, 1993; U.S. Pat. No. 5,387,748 issued Feb. 7, 1995; U.S. Pat. No. 5,491,139 issued Feb. 13, 1996; U.S. Pat. No. 5,530,116 issued Jun. 25, 1996; and EPO publications 0366189 published May 2, 1990 and 0366640 published May 2, 1990, all incorporated herein by reference. For compositions and methods of use, the compounds of formula Q-L-B are useful in the same way as compound of Formula 1. Thus, they can be interchanged in the composition examples herein.

Biological activities of the invention compounds can be compared to ciprofloxacin and the other known antimicrobial quinolone compounds. Compounds of the subject invention provide better antibacterial properties against certain quinolone resistant bacteria compared to ciprofloxacin and certain other prior art compounds. When tested against quinolone-resistant bacteria such as *S. aureus, S. saprophyticus, E. faecalis, S. pyogenes, S. pneumoniae, S. viridans, E. coli, P. aeruginosa, P. mirabilis, K. pneumoniae, E. cloacae*, certain compounds of the subject invention have been found to have MIC values (μg/ml) that are up to about 500 times lower than ciprofloxacin.

The compounds of the present invention also have lowered phototoxicity compared to previously disclosed 8-halogen quinolones such as Clinafloxacin. One skilled in the art will appreciate how to measure phototoxicity, for example, Horst Spielmann et al, "A Study on UV Filter Chemicals from Annex VI of European Union Directive 76/768/EEC in the In Vitro 3T3 NRU Phototoxicity Test", ATLA, Vol. 26, pp 679-708, (1998), which is incorporated herein by reference.

Methods of Making the Compounds

In making the compounds of the invention, the order of synthetic steps may be varied to increase yield of desired product. In addition, the skilled artisan will also recognize the judicious choice of reactants, solvents, and temperatures is an important component in successful synthesis. While the determination of optimal conditions, etc. is routine, it will be understood that a variety of compounds can be generated in a similar fashion, using the guidance of the scheme below.

The starting materials used in preparing the compounds of the invention are known, made by known methods, or are commercially available as a starting material.

It is recognized that the skilled artisan in the art of organic chemistry can readily carry out standard manipulations of organic compounds without further direction; that is, it is well within the scope and practice of the skilled artisan to carry out such manipulations. These include, but are not limited to, reduction of carbonyl compounds to their corresponding alcohols, oxidations, acylations, aromatic substitutions, both electrophilic and nucleophilic, etherifications, esterification and saponification and the like. Examples of these manipulations are discussed in standard texts such as March, *Advanced Organic Chemistry* (Wiley), Carey and Sundberg, *Advanced Organic Chemistry* (Vol. 2), Fieser & Feiser, *Reagents for Organic Synthesis* (16 volumes), L. Paquette, *Encyclopedia of Reagents for Organic Synthesis* (8 volumes), Frost & Fleming, *Comprehensive Organic Synthesis* (9 volumes) and the like.

The skilled artisan will readily appreciate that certain reactions are best carried out when other functionality is masked or protected in the molecule, thus avoiding any undesirable side reactions and/or increasing the yield of the reaction. Often the skilled artisan utilizes protecting groups to accomplish such increased yields or to avoid the undesired reactions. These reactions are found in the literature and are also well within the scope of the skilled artisan. Examples of many of these manipulations can be found for example in T. Greene, *Protecting Groups in Organic Synthesis*. Of course, amino acids used as starting materials with reactive side chains are preferably blocked to prevent undesired side reactions.

General procedures for preparing quinolone moieties useful in making the compounds of the subject invention are described in the following references, all incorporated by reference herein (including articles listed within these references); *Progress in Drug Research*, Vol. 21, pp. 9-104 (1977); *J. Med. Chem.*, Vol. 23, pp. 1358-1363 (1980); *J. Med. Chem.*, Vol. 29, pp. 2363-2369 (1986); *J. Med. Chem.*, Vol. 31, p. 503 (1988); *J. Med. Chem.*, Vol. 31, pp. 503-506 (1988); *J. Med. Chem.*, Vol. 31, pp. 983-991 (1988); *J. Med. Chem.*, Vol. 31, pp. 991-1001 (1988); *J. Med. Chem.*, Vol. 31, pp. 1586-1590 (1988); *J. Med. Chem.*, Vol. 31, pp. 1598-1611 (1988); *J. Med. Chem.*, Vol. 32, pp. 537-542 (1989); *J. Med. Chem.*, Vol. 32, p. 1313 (1989); *J. Med. Chem.*, Vol. 32, pp. 1313-1318 (1989); *Drugs Exptl. Clin. Res.*, Vol. 14, pp. 379-383 (1988); *J. Pharm. Sci.*, Vol. 78, pp. 585-588 (1989); *J. Het. Chem.*, Vol. 24, pp. 181-185 (1987); *J. Het. Chem.*, Vol. 25, pp. 479-485 (1988); *Chem. Pharm. Bull.*, Vol. 35, pp. 2281-2285 (1987); *Chem. Pharm. Bull.*, Vol. 36, pp. 1223-1228 (1988); U.S. Pat. No. 4,594,347, Jun. 10, 1986; U.S. Pat. No. 4,599,334, Jul. 8, 1986; U.S. Pat. No. 4,687,770, Aug. 1, 1987; U.S. Pat. No. 4,689,325, Aug. 25, 1987; U.S. Pat. No. 4,767,762, Aug. 30, 1988; U.S. Pat. No. 4,771,055, Sep. 13, 1988; U.S. Pat. No. 4,795,751, Jan. 3, 1989; U.S. Pat. No. 4,822,801, Apr. 18, 1989; U.S. Pat. No. 4,839,355, Jun. 13, 1989; U.S. Pat. No. 4,851,418, Jul. 25, 1989; U.S. Pat. No. 4,886,810, Dec. 12, 1989; U.S. Pat. No. 4,920,120, Apr. 24, 1990; U.S. Pat. No. 4,923,879, May 8, 1990; U.S. Pat. No. 4,954,507, Sep. 4, 1990; U.S. Pat. No. 4,956,465, Sep. 11, 1990; U.S. Pat. No. 4,977,154, Dec. 11, 1990; U.S. Pat. No. 4,980,470, Dec. 25, 1990; U.S. Pat. No. 5,013,841, May 7, 1991; U.S. Pat. No. 5,045,549, Sep. 3, 1991; U.S. Pat. No. 5,290,934, Mar. 1, 1994; U.S. Pat. No. 5,328,908, Jul. 12, 1994; U.S. Pat.

No. 5,430,152, Jul. 4, 1995; European Patent Publication 172,651, Feb. 26, 1986; European Patent Publication 230, 053, Jul. 29, 1987; European Patent Publication 230,946, Aug. 5, 1987; European Patent Publication 247,464, Dec. 2, 1987; European Patent Publication 284,935, Oct. 5, 1988; European Patent Publication 309,789, Apr. 5, 1989; European Patent Publication 332,033, Sep. 13, 1989; European Patent Publication 342,649, Nov. 23, 1989; and Japanese Patent Publication 09/67,304 (1997).

The compounds are generally made by methods which include those disclosed in the references above. A preferred method is to prepare the quinolone moiety with a suitable leaving group at the 7 position and have that leaving group displaced by the heterocycle-X as a last step. Examples of these methods follow.

The quinolone compounds of the subject invention may be prepared several ways. Versatile methodologies for providing the compounds of the invention are shown in Scheme I below:

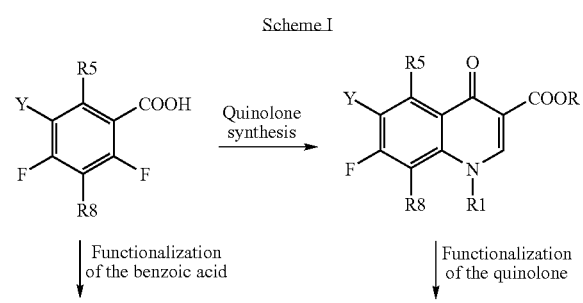

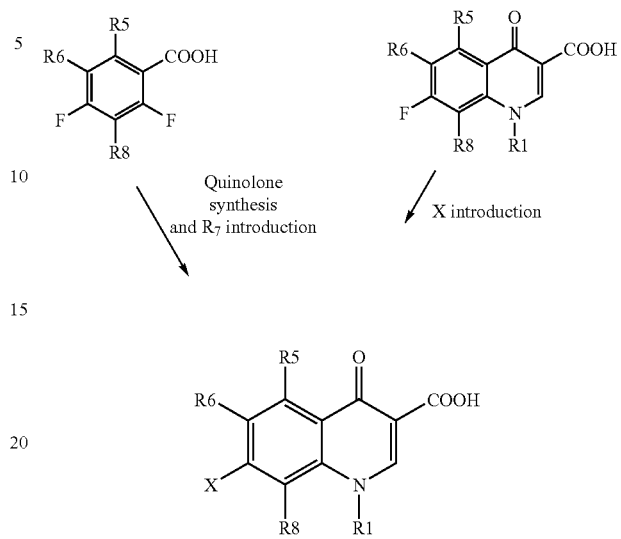

In Scheme I, Y can be bromo, iodo, nitro, amino, acetyl, or like moieties known to the skilled chemist; preferred Y is bromo or nitro.

Alternatively, the general methodology of Scheme II can be used to make certain subject compounds.

EXAMPLE A

Preparation of 7-[3R-(1-amino-methylethylpyrrolidinyl)]-1-cyclopropyl-1,4-dihydro-8-chloro-6-hydroxy-4-oxo-3-quinolinecarboxylic acid sulfate Synthetic Pathway:

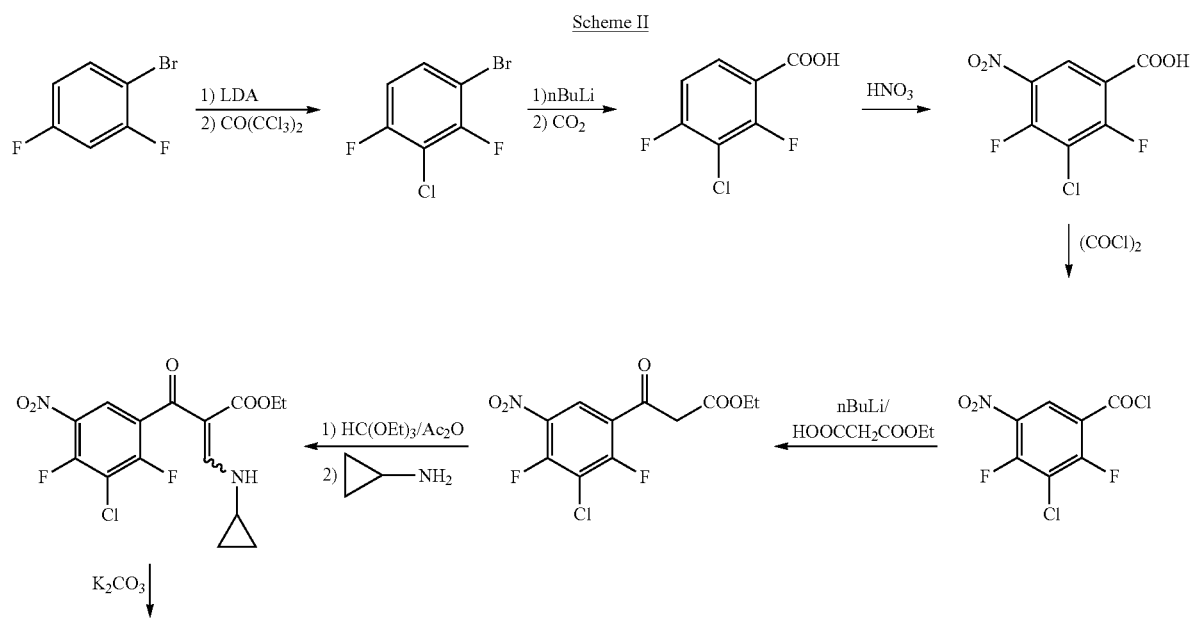

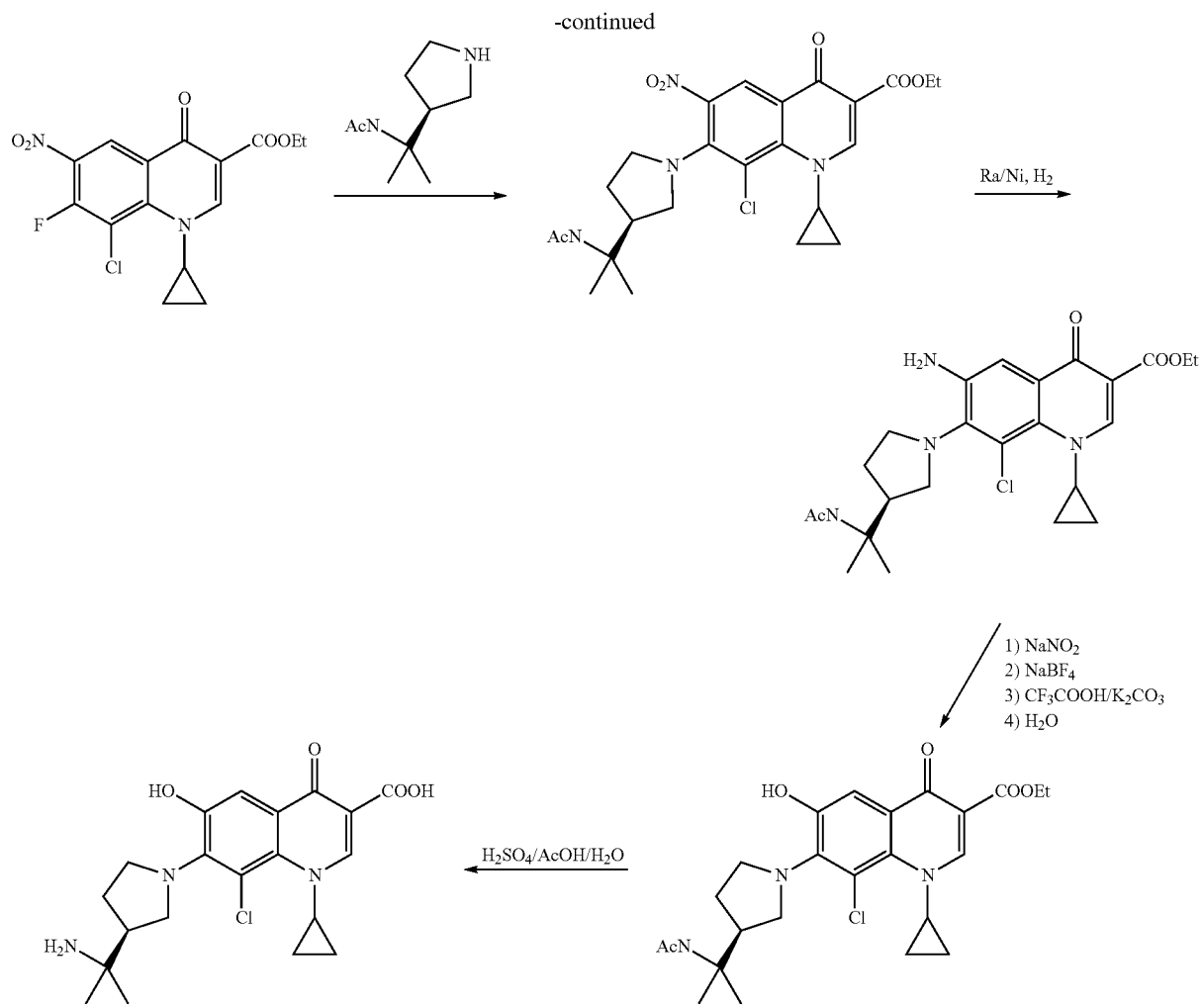

Procedures:

3-Chloro-2,4-difluoro-bromobenzene

To a solution of 19 ml (0.135 mole) of diisopropylamine in 125 ml of tetrahydrofuran (THF) cooled at −20° C. is added 80 ml of n-butyllithium (1.6 M in hexane). The temperature is raised to 0° C. for 5 minutes and lowered to −78° C. Then 25 g (0.129 mole) of 2,4-difluoro-bromobenzene is then added and the reaction is stirred at −65° C. for 2 hours. Then, 25 ml (0.164 mole) of hexachloroacetone is added and the solution is warmed at room temperature. After evaporation of the solvent, the residue is distilled under vacuum to give the desired product.

3-Chloro-2,4-difluorobenzoic acid

To a solution of 21.5 g (0.0945 mole) of 3-chloro-2,4-difluoro-bromobenzene in 220 ml of ether at −78° C. is added 59 ml of 1.6 M n-butyllithium diluted in 60 ml of ether keeping the temperature below −70° C. After 15 minutes, $CO_2$ is bubbled in the reaction keeping the temperature below −70° C. After warming to room temperature, water and hydrochloric acid are added and the organic phase separated, and dried. Removal of the solvent affords the desired product.

5-Nitro-3-chloro-2,4-difluorobenzoic acid

An amount of 1 g of 3-chloro-2,4-difluorobenzoic acid is added to a mixture of 1 ml of fuming nitric acid and 1.3 ml of sulfuric acid at 0° C. The suspension is then stirred at room temperature for 30 minutes and poured on ice. Filtration affords the desired product.

5-Nitro-3-chloro-2,4-difluorobenzoyl chloride

An amount of 3.47 g (0.015 mole) of 5-nitro-3-chloro-2,4-difluorobenzoic acid and 2.03 g (0.016 mole) of oxalyl chloride are dissolved in 15 ml of dichloromethane then two drops of DMF are added. The reaction is stirred for 14 hours then the solvent is evaporated under vacuum to afford the desired product.

Ethyl 5-nitro-3-chloro-2,4-difluoro-benzoyl acetate

An amount of 3.26 g (0.0195 mole) of monoethyl malonate is dissolved in 10 ml of THF and the solution is cooled at −50° C. A quantity of 30 ml of 1.6M n-Butyllithium is added over a period of 30 minutes. A solution of 3.35 g (0.013 mole) of 5-nitro-3-chloro-2,4-difluorobenzoyl chloride in solution in 2 ml of THF is then added keeping the temperature below −50° C. The reaction is then stirred at room temperature for 3 hours and 5 ml of 1N HCl are added. The organic layer is separated and the aqueous phase extracted with ethyl acetate. The combined organic phases are dried and the crude desired product obtained after evaporation of the solvent. The pure product is obtained after chromatography using dichloromethane and ethyl acetate (95/5.)

Ethyl 3-cyclopropylamino-2-(2,4-difluoro-3-chloro-5-nitro-benzoyl) acrylate

An amount of 0.205 g (0.0067 mole) of ethyl 5-nitro-3chloro-2,4-difluoro-benzoyl acetate is dissolved in a mixture of 0.17 ml of triethyl orthoformate and 0.3 ml of acetic anhydride. The reaction mixture is warmed at 120° C. for 3 hours and the remaining reagents are removed under vacuum. The residue is dissolved in 2 ml of ethanol and the solution is cooled at −5° C. A quantity of 0.044 ml (0.0064 mole) of cyclopropylamine is added and the desired product isolated by filtration.

Ethyl 1-cyclopropyl-1,4-dihydro-7-fluoro-8-chloro-6-nitro-4-oxo-quinoline-3-carboxylate An amount of 0.088 g of ethyl 3-cyclopropylamino-2-(2,4-difluoro-3-chloro-5-nitro-benzoyl) acrylate is dissolved in 1 ml of ethyl acetate at 0° C. A quantity of 0.1 g of potassium carbonate is added. The desired product precipitates and is isolated by filtration.

Ethyl 7-[3R-(1-acetylamino-methylethylpyrrolidinyl)]-1-cyclopropyl-1,4-dihydro-8-chloro-6-nitro-4-oxo-3-quinolinecarboxylate An amount of 0.064 g of ethyl 1-cyclopropyl-1,4-dihydro-7-fluoro-8-chloro-6-nitro-4-oxo-quinoline-3-carboxylate and 0.08 g of 3R-(1-acetylamino-methylethylpyrrolidine are dissolved in 1 ml of DMSO and stirred at room temperature for 15 minutes. A quantity of 5 ml of water is then added and the desired product collected by filtration.

Ethyl 7-[3R-(1-acetylamino-methylethylpyrrolidinyl)]-1-cyclopropyl-1,4-dihydro-8-chloro-6-amino-4-oxo-3-quinolinecarboxylate An amount of 0.072 g of ethyl 7-[3R-(1-acetylamino-methylethylpyrrolidinyl)]-1-cyclopropyl-1,4-dihydro-8-chloro-6-nitro-4-oxo-3-quinolinecarboxylate is dissolved in 1 ml of ethanol and 0.035 g of Raney Nickel is added. The reaction mixture is stirred under hydrogen for 18 hours. The solid is removed by filtration on Celite and the filtrate evaporated to give the desired product.

Ethyl 7-[3R-(1-acetylamino-methylethylpyrrolidinyl)]-1-cyclopropyl-1,4-dihydro-8-chloro-6-hydroxy-4-oxo-3-quinolinecarboxylate An amount of 0.055 g of ethyl 7-[3R-(1-acetylamino-methylethylpyrrolidinyl)]-1-cyclopropyl-1,4-dihydro-8-chloro-6-amino-4-oxo-3-quinolinecarboxylate is dissolved in 2 ml of 2N HCl at 0° C. A solution of 0.01 g of sodium nitrite in 0.2 ml of water is then added and the solution stirred at 0° C. for 1 hour. A quantity of 0.02 g of NaBF4 in solution in 0.2 ml of water is then added and the resulting precipitate filtered. The solid is re-suspended in 2 ml of trifluoroacetic acid and 0.5 g of K$_2$CO$_3$ added by portion at 40° C. Water (10 ml) is then added and the reaction mixture allowed to stir at room temperature for 2 hours. The aqueous phase is extracted with dichloromethane and the desired product purified by chromatography using dichloromethane/methanol 95/5 as solvent.

7-[3R-(1-amino-methylethylpyrrolidinyl)]-1-cyclopropyl-1,4-dihydro-8-chloro-6-hydroxy-4-oxo-3-quinolinecarboxylic acid sulfate An amount of 0.022 g of ethyl 7-[3R-(1-acetylamino-methylethylpyrrolidinyl)]-1-cyclopropyl-1,4-dihydro-8-chloro-6-hydroxy-4-oxo-3-quinolinecarboxylate is suspended in 0.5 ml of a 6/4/1 mixture of acetic acid/sulfuric acid/water and the reaction mixture is refluxed for 4 hours. After cooling the desired product is isolated by filtration.

Compositions of the Invention

The compositions of this invention comprise:
(a) a safe and effective amount of the compound of the invention
(b) a pharmaceutically-acceptable excipient.

It may also optionally comprise other antimicrobials or other actives, which may or may not act synergistically with the invention.

A "safe and effective amount" of a quinolone is an amount that is effective, to inhibit microbial growth at the site of an infection to be treated in a host, without undue adverse side effects (such as toxicity, irritation, or allergic response), commensurate with a reasonable benefit/risk ratio when used in the manner of this invention. The specific "safe and effective amount" will vary with such factors as the particular condition being treated, the physical condition of the patient, the duration of treatment, the nature of concurrent therapy (if any), the specific dosage form to be used, the excipient employed, the solubility of the quinolone therein, and the dosage regimen desired for the composition.

The compositions of this invention are preferably provided in unit dosage form. As used herein, a "unit dosage form" is a composition of this invention containing an amount of a quinolone that is suitable for administration to a human or lower animal subject, in a single dose, according to good medical practice. These compositions preferably contain from about 30 mg, more preferably from about 50 mg, more preferably still from about 100 mg, preferably to about 20,000 mg, more preferably to about 7,000 mg, more preferably still to about 1,000 mg, most preferably to about 500 mg, of a quinolone.

The compositions of this invention may be in any of a variety of forms, suitable (for example) for oral, rectal, topical or parenteral administration. Depending upon the particular route of administration desired, a variety of pharmaceutically-acceptable excipients well-known in the art may be used. These include solid or liquid fillers, diluents, hydrotropes, surface-active agents, and encapsulating substances. Optional pharmaceutically-active materials may be included, which do not substantially interfere with the antimicrobial activity of the quinolone. The amount of excipient employed in conjunction with the quinolone is sufficient to provide a practical quantity of material for administration per unit dose of the quinolone. Techniques and compositions for making dosage forms useful in the methods of this invention are described in the following references, all incorporated by reference herein: *Modern Pharmaceutics*, Vol. 7, Chapters 9 and 10 (Banker & Rhodes, editors, 1979); Lieberman et al., *Pharmaceutical Dosage Forms: Tablets* (1981); and Ansel, *Introduction to Pharmaceutical Dosage Forms* 2d Edition (1976).

In particular, pharmaceutically-acceptable excipients for systemic administration include sugars, starches, cellulose and its derivatives, malt, gelatin, talc, calcium sulfate, vegetable oils, synthetic oils, polyols, alginic acid, phosphate buffer solutions, emulsifiers, isotonic saline, and pyrogen-free water. Preferred excipients for parenteral administration include propylene glycol, ethyl oleate, pyrrolidone, ethanol, and sesame oil. Preferably, the pharmaceutically-acceptable excipient, in compositions for parenteral administration, comprises at least about 90% by weight by the total composition.

In addition, dosages for injection may be prepared in dried or lyophilized form. Such forms can be reconstituted with water or saline solution, depending on the preparation of the dosage form. Such forms may be packaged as individual dosages or multiple dosages for easier handling. Where lyophilized or dried dosages are used, the reconstituted dosage form is preferably isotonic, and at a physiologically compatible pH.

Various oral dosage forms can be used, including such solid forms as tablets, capsules, granules and bulk powders. These oral forms comprise a safe and effective amount, usually at least about 5%, and preferably from about 25% to about 50%, of the quinolone. Tablets can be compressed, tablet triturates, enteric-coated, sugar-coated, film-coated, or multiple-compressed, containing suitable binders, lubricants, diluents, disintegrating agents, coloring agents, flavoring agents, flow-inducing agents, and melting agents. Liquid oral dosage forms include aqueous solutions, emulsions, suspensions, solutions and/or suspensions reconstituted from non-effervescent granules, and effervescent preparations reconstituted from effervescent granules, containing suitable solvents, preservatives, emulsifying agents, suspending agents, diluents, sweeteners, melting agents, coloring agents and flavoring agents, such are well known to the skilled artisan. Preferred excipients for oral administration include gelatin, propylene glycol, cottonseed oil and sesame oil.

The compositions of this invention can also be administered topically to a subject, i.e., by the direct laying on or spreading of the composition on the epidermal or epithelial tissue of the subject. Such compositions include, for example, lotions, creams, solutions, gels and solids. These topical compositions preferably comprise a safe and effective amount, usually at least about 0.1%, and preferably from about 1% to about 5%, of the quinolone. Suitable excipients for topical administration preferably remain in place on the skin as a continuous film, and resist being removed by perspiration or immersion in water. Generally, the excipient is organic in nature and capable of having dispersed or dissolved therein the quinolone. The excipient may include pharmaceutically-acceptable emollients, emulsifiers, thickening agents, and solvents and the like; these are well known to the skilled artisan.

Methods of Using the Compounds

This invention also provides methods of treating or preventing an infectious disorder in a human or other animal subject, by administering a safe and effective amount of a quinolone to said subject. As used herein, an "infectious disorder" is any disorder characterized by the presence of a microbial infection. Preferred methods of this invention are for the treatment of bacterial infections. Such infectious disorders include (for example) central nervous system infections, external ear infections, infections of the middle ear (such as acute otitis media), infections of the cranial sinuses, eye infections, infections of the oral cavity (such as infections of the teeth, gums and mucosa), upper respiratory tract infections, lower respiratory tract infections, including pneumonia, genitourinary infections, gastrointestinal infections, gynecological infections, septicemia, sepsis, peritonitis, bone and joint infections, skin and skin structure infections, bacterial endocarditis, burns, antibacterial prophylaxis of surgery, and antibacterial prophylaxis in post-operative patients or in immunosuppressed patients (such as patients receiving cancer chemotherapy, or organ transplant patients).

The quinolone derivatives and compositions of this invention can be administered topically or systemically. Systemic application includes any method of introducing the quinolone into the tissues of the body, e.g., intrathecal, epidural, intramuscular, transdermal, intravenous, intraperitoneal, subcutaneous, sublingual, rectal, and oral administration. The specific dosage of antimicrobial to be administered, as well as the duration of treatment, are mutually dependent. The dosage and treatment regimen will also depend upon such factors as the specific quinolone used, the resistance pattern of the infecting organism to the quinolone used, the ability of the quinolone to reach minimum inhibitory concentrations at the site of the infection, the nature and extent of other infections (if any), the personal attributes of the subject (such as weight), compliance with the treatment regimen, the age and health status of the patient, and the presence and severity of any side effects of the treatment.

Typically, for a human adult (weighing approximately 70 kilograms), from about 75 mg, more preferably from about 200 mg, most preferably from about 500 mg to about 30,000 mg, more preferably to about 10,000 mg, most preferably to about 3,500 mg, of quinolone is administered per day. Treatment regimens preferably extend from about 1, preferably from about 3 to about 56 days, preferably to about 20 days, in duration. Prophylactic regimens (such as avoidance of opportunistic infections in immunocompromised patients) may extend 6 months, or longer, according to good medical practice.

A preferred method of parenteral administration is through intravenous injection. As is known and practiced in the art, all formulations for parenteral administration must be sterile. For mammals, especially humans, (assuming an approximate body weight of 70 kilograms) individual doses of from about 100 mg, preferably from about 500 mg to about 7,000 mg, more preferably to about 3,500 mg, is acceptable.

In some cases, such as generalized, systemic infections or in immune-compromised patients, the invention may be dosed intravenously. The dosage form is generally isotonic and at physiological pH. The dosage amount will depend on the patient and severity of condition, as well as other commonly considered parameters. Determination of such doses is well within the scope of practice for the skilled practitioner using the guidance given in the specification.

A preferred method of systemic administration is oral administration. Individual doses of from about 20 mg, more preferably from about 100 mg to about 2,500 mg, more preferably to about 500 mg.

Topical administration can be used to deliver the quinolone systemically, or to treat a local infection. The amounts of quinolone to be topically administered depends upon such factors as skin sensitivity, type and location of the tissue to be treated, the composition and excipient (if any) to be administered, the particular quinolone to be administered, as well as the particular disorder to be treated and the extent to which systemic (as distinguished from local) effects are desired.

The following non-limiting examples illustrate the compounds, compositions, processes, and uses of the present invention.

Composition Example I

A tablet composition for oral administration, according to the present invention, is made comprising:

| Component | Amount |
| --- | --- |
| Compound of Example 12 | 150 mg |
| Lactose | 120 mg |

-continued

| Component | Amount |
|---|---|
| Maize Starch | 70 mg |
| Talc | 4 mg |
| Magnesium Stearate | 1 mg |

Other compounds having a structure according to Formula I are used with substantially similar results.

Composition Example II

A capsule containing 200 mg of active for oral administration, according to the present invention, is made comprising:

| Component | Amount (% w/w) |
|---|---|
| Compound of Example 13 | 15% |
| Hydrous Lactose | 43% |
| Microcrystalline Cellulose | 33% |
| Crosspovidone | 3.3% |
| Magnesium Stearate | 5.7% |

Other compounds having a structure according to Formula I are used with substantially similar results.

Composition Example III

A saline-based composition for ocular administration, according to the present invention, is made comprising:

| Component | Amount (% w/w) |
|---|---|
| Compound of Example 16 | 10% |
| Saline | 90% |

Other compounds having a structure according to Formula I are used with substantially similar results.

Composition Example IV

A intranasal composition for local administration, according to the present invention, is made comprising:

| Component | Composition (% w/v) |
|---|---|
| Compound of Example 30 | 0.20 |
| Benzalkonium chloride | 0.02 |
| EDTA | 0.05 |
| Glycerin | 2.0 |
| PEG 1450 | 2.0 |
| Aromatics | 0.075 |
| Purified water | q.s. |

Other compounds having a structure according to Formula 1 are used with substantially similar results.

Composition Example V

A inhalation aerosol composition, according to the present invention, is made comprising:

| Component | Composition (% w/v) |
|---|---|
| Compound of Example 47 | 5.0 |
| Ascorbic acid | 0.1 |
| Menthol | 0.1 |
| Sodium Saccharin | 0.2 |
| Propellant (F12, F114) | q.s. |

Other compounds having a structure according to Formula 1 are used with substantially similar results.

Composition Example VI

A topical opthalmic composition, according to the present invention, is made comprising:

| Component | Composition (% w/v) |
|---|---|
| Compound of Example 63 | 0.10 |
| Benzalkonium chloride | 0.01 |
| EDTA | 0.05 |
| Hydroxyethylcellulose | 0.5 |
| Acetic acid | 0.20 |
| Sodium metabisulfite | 0.10 |
| Sodium chloride (0.9%) | q.s. |

Other compounds having a structure according to Formula 1 are used with substantially similar results.

Composition Example VII

An antimicrobial composition for parenteral administration, according to this invention is made comprising:

| Component | Amount |
|---|---|
| Compound of Example 84 | 30 mg/ml excipient |
| Excipient: | |
| 50 mm phosphate buffer pH 5 buffer with lecithin | 0.48% |
| carboxymethylcellulose | 0.53 |
| povidone | 0.50 |
| methyl paraben | 0.11 |
| propyl paraben | 0.011 |

The above ingredients are mixed, forming a suspension. Approximately 2.0 ml of the suspension is systemically administered, via intramuscular injection, to a human subject suffering from a lower respiratory tract infection, with *Streptococcus pneumoniae* present. This dosage is repeated twice daily, for approximately 14 days. After 4 days, symptoms of the disease subside, indicating that the pathogen has been substantially eradicated. Other compounds having a structure according to Formula 1 are used with substantially similar results.

Composition Example VIII

An enteric coated antimicrobial composition for oral administration, according to this invention, is made comprising the following core tablet:

| Component | Amount (mg) |
|---|---|
| Compound of Example 105 | 350.0 |
| Maltodextrine | 30.0 |
| Magnesium Stearate | 5.0 |
| Microcrystalline Cellulose | 100.0 |
| Colloidal Silicon Dioxide | 2.5 |
| Povidone | 12.5 |

The components are admixed into a bulk mixture. Compressed tablets are formed, using tabletting methods known in the art. The tablet is then coated with a suspension of methacrylic acid/methacrylic acid ester polymer in isopropanol/acetone. A human subject, having a urinary tract infection with *Escherichia coli* present, is orally administered two of the tablets, every 8 hours, for 4 days. Symptoms of the disease then subside, indicating substantial eradication of the pathogen. Other compounds having a structure according to Formula 1 are used with substantially similar results.

All references described herein are hereby incorporated by reference.

While particular embodiments of the subject invention have been described, it will be obvious to those skilled in the art that various changes and modifications of the subject invention can be made without departing from the spirit and scope of the invention. It is intended to cover, in the appended claims, all such modifications that are within the scope of this invention.

What is claimed is:

1. A compound having the following formula:

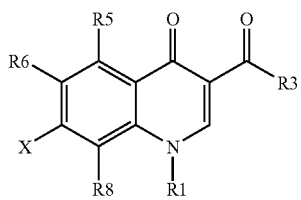

wherein:
(a) X is selected from the group consisting of

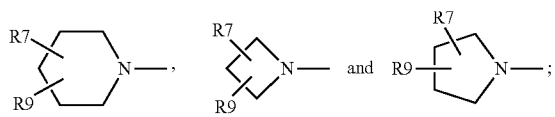

(b) R1 is selected from the group consisting of $C_3$ to $C_5$ cycloalkyl, $C_1$ to $C_2$ alkanyl, $C_2$ to $C_3$ linear alkenyl, $C_3$ to $C_4$ branched alkanyl or alkenyl, all such alkyl or cycloalkyl moieties being unsubstituted or substituted with from 1 to 3 fluoro; and phenyl, unsubstituted or substituted with from 1 to 3 fluoro, or with one hydroxy in the 4-position;
(c) R3 is hydrogen or hydroxy;
(d) R5 is selected from the group consisting of hydrogen, hydroxy, amino, halo, $C_1$ to $C_2$ alkanyl, $C_2$ alkenyl, and methoxy, all such alkyl and methoxy moieties being unsubstituted or substituted with from 1 to 3 fluoro;
(e) R6 is hydrogen;
(f) R8 is selected from the group consisting of chloro, bromo, methoxy, methylthio, $C_1$ to $C_2$ alkanyl, $C_2$ to $C_4$ alkenyl, all such alkyl, methoxy and methylthio moieties being unsubstituted or substituted with from 1 to 3 fluoro;
(g) R7 is amino which is attached to a ring carbon of X which is not adjacent to the ring nitrogen, the amino being unsubstituted or substituted with one or two $C_1$ to $C_3$ alkanyl; or aminoalkanyl which is attached to any ring carbon of X and is $C_1$ to $C_3$ alkanyl substituted with one amino, the amino being unsubstituted or substituted with one or two $C_1$ to $C_3$ alkanyl;
(h) each R9 is independently selected from the group consisting of hydrogen, $C_1$ to $C_4$ alkanyl, $C_2$ to $C_6$ alkenyl or alkynyl, and a $C_3$ to $C_6$ fused or spirocycle alkyl ring, all such alkyl moieties being unsubstituted or substituted with from 1 to 3 fluoro; and
(j) a R7 moiety described in (g) and a R9 moiety described in (h) may optionally be connected thus forming a fused or spirocycle ring with the N-containing ring shown in (a), the fused or spirocycle ring comprising from 2 to 5 ring carbons and 0 or 1 ring nitrogen, but if such rings are fused, R8 is other than chloro or bromo;

an optical isomer, diastereomer or enantiomer thereof; a pharmaceutically-acceptable salt, hydrate, or biohydrolyzable ester, amide or imide thereof.

2. The compound of claim 1 wherein R3 is hydroxy.

3. The compound of claim 2 wherein:
(a) X is

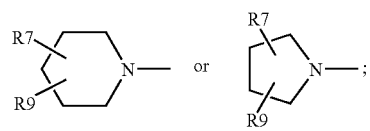

(b) R1 is selected from the group consisting of $C_3$ to $C_5$ cycloalkanyl, methyl, ethyl, ethenyl, isopropyl, isopropenyl, isobutyl, isobutenyl, t-butyl, all such alkyl or cycloalkanyl moieties being unsubstituted or substituted with from 1 to 3 fluoro; and phenyl, unsubstituted or substituted with from 1 to 3 fluoro, or with one hydroxy in the 4-position;
(c) R5 is selected from the group consisting of hydrogen, hydroxy, amino, fluoro, chloro, bromo, and methyl, the methyl being unsubstituted or substituted with from 1 to 3 fluoro;
(d) R8 is selected from the group consisting of chloro, bromo, methoxy or methylthio unsubstituted or substituted with from 1 to 3 fluoro, and methyl unsubstituted or substituted with from 1 to 3 fluoro;
(e) R7 is attached to a ring carbon of X which is not adjacent to the ring nitrogen; and
(f) no more than two ring carbons of X have non-hydrogen R9's attached thereto.

4. The compound of claim 3 wherein, if R8 is unsubstituted alkyl, R7 is aminoalkanyl.

5. The compound of claim 3 wherein R7 is amino unsubstituted or substituted with one $C_1$ to $C_3$ alkanyl or two methyl, or aminoalkanyl which is methyl or ethyl or isopropyl substituted with one amino unsubstituted or substituted with one methyl or ethyl or dimethyl; and any non-hydrogen R9 are methyl or ethyl.

6. The compound of claim 5 wherein R1 is selected from the group consisting of cyclopropyl, ethyl, phenyl substituted with 1 to 3 fluoro, and 4-hydroxyphenyl.

7. The compound of claim 6 wherein R5 is selected from the group consisting of hydrogen, hydroxy, chloro, bromo, amino, and methyl, the methyl being unsubstituted or substituted with from 1 to 3 fluoro.

8. The compound of claim 7 wherein R8 is selected from the group consisting of chloro, methoxy, methylthio, monofluoromethyl, difluoromethyl, and trifluoromethyl.

9. The compound of claim 7 wherein R7 is selected from the group consisting of amino, methylamino, aminomethyl, methylaminomethyl, 1-aminoethyl, 1-methylamino ethyl, 1-amino-1-methylethyl and 1-methyamino-1-methylethyl.

10. The compound of claim 9 wherein R1 is cyclopropyl or ethyl, unsubstituted or substituted with from 1 to 3 fluoro.

11. The compound of claim 8, wherein R8 is methoxy or methylthio.

12. The compound of claim 11 wherein R5 is selected from the group consisting of hydrogen, hydroxy, amino, and methyl.

13. The compound of claim 12 wherein R1 is cyclopropyl.

14. The compound of claim 12 wherein R1 is ethyl.

15. The compound of claim 14 wherein R5 is hydrogen.

16. The compound of claim 3, 9, 13 or 14 wherein R8 is methoxy.

17. The compound of claim 3, 9, 13 or 14 wherein X comprises the pyrrolidinyl ring.

18. The compound of claim 3, 9, 13 or 14 wherein X comprises the pyrrolidinyl ring, and R7 is selected from the group consisting of aminomethyl, methylaminomethyl, 1-aminoethyl, 1-methylaminoethyl, 1-amino-1-methylethyl and 1-methyamino-1-methylethyl.

19. The compound of claim 3, 9, 13 or 14 wherein X comprises the piperidinyl ring.

20. The compound of claim 3, 9, 13 or 14 wherein X comprises the piperidinyl ring, and R7 is amino or methylamino.

21. The compound of claim 3, 9, 13 or 14 wherein all R9 are hydrogen or only one ring carbon of X has non-hydrogen R9, such non-hydrogen R9 being selected from methyl, ethyl, dimethyl and spirocyclopropyl.

22. The compound of claim 3, 9, 13 or 14 wherein X comprises the pyrrolidinyl ring, and R9 comprises alkyl or dialkyl on a ring carbon of the pyrrolidinyl ring which is adjacent to the ring nitrogen.

23. A compound selected from the group consisting of:
7-[3-aminopiperidinyl]-1-cyclopropyl-1,4-dihydro-8-methoxy-4-oxo-3-quinolinecarboxylic acid;
7-[3-methylaminopiperidinyl]-1-cyclopropyl-1,4-dihydro-8-methoxy-4-oxo-3-quinolinecarboxylic acid;
7-[3-amino-4-methyl-piperidinyl]-1-cyclopropyl-1,4-dihydro-8-methoxy-4-oxo-3-quinolinecarboxylic acid;
7-[3-amino-4-ethyl-piperidinyl]-1-cyclopropyl-1,4-dihydro-8-methoxy-4-oxo-3-quinolinecarboxylic acid;
7-[3-amino-6,6-dimethyl-piperidinyl]-1-cyclopropyl-1,4-dihydro-8-methoxy-4-oxo-3-quinolinecarboxylic acid;
7-[3-amino-6-methyl-piperidinyl]-1-cyclopropyl-1,4-dihydro-8-methoxy-4-oxo-3-quinolinecarboxylic acid;
7-[6-amino-4-azaspiro[2.5]-octanyl]-1-cyclopropyl-1,4-dihydro-8-methoxy-4-oxo-3-quinolinecarboxylic acid;
7-[7-amino-5-azaspiro[2.5]-octanyl]-1-cyclopropyl-1,4-dihydro-8-methoxy-4-oxo-3-quinolinecarboxylic acid;
7-[4-amino-6-azaspiro[2.5]-octanyl]-1-cyclopropyl-1,4-dihydro-8-methoxy-4-oxo-3-quinolinecarboxylic acid;
or a pharmaceutically-acceptable salt thereof.

24. A compound which is 7-[3S-amino-5S-methyl-piperidinyl]-1-cyclopropyl-1,4-dihydro-8-methoxy-4-oxo-3-quinolinecarboxylic acid or pharmaceutically acceptable salt thereof.

25. A pharmaceutical composition comprising:
(a) a safe and effective amount of a compound of any of claim 3, 9, 13, 14, 23 or 24; and
(b) a pharmaceutically-acceptable excipient.

26. A method for preventing or treating microbial infection comprising administering to a host in need of such a treatment a safe and antimicrobially effective amount of a compound of any of claim 3, 9, 13, 14, 23 or 24.

* * * * *